United States Patent
Zhang et al.

(10) Patent No.: US 11,024,427 B2
(45) Date of Patent: *Jun. 1, 2021

(54) PRIVACY-COMPLIANT ANALYSIS OF HEALTH BY TRANSACTION DATA

(71) Applicant: MasterCard International Incorporated, Purchase, NY (US)

(72) Inventors: Tong Zhang, Greenwich, CT (US); Qian Wang, Ridgefield, CT (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 963 days.

This patent is subject to a terminal disclaimer.

(21) Appl. No.: 15/656,750

(22) Filed: Jul. 21, 2017

(65) Prior Publication Data

US 2017/0323077 A1 Nov. 9, 2017

Related U.S. Application Data

(63) Continuation of application No. 14/133,081, filed on Dec. 18, 2013, now Pat. No. 9,747,419.

(51) Int. Cl.
*G16H 50/30* (2018.01)
*G06Q 40/00* (2012.01)
*G16H 50/80* (2018.01)
*G06F 19/00* (2018.01)
*G06Q 10/10* (2012.01)

(52) U.S. Cl.
CPC .............. *G16H 50/30* (2018.01); *G06F 19/00* (2013.01); *G06Q 10/10* (2013.01); *G06Q 40/12* (2013.12); *G16H 50/80* (2018.01)

(58) Field of Classification Search
CPC ............... G06F 19/328; G06F 19/3456; G06F 2221/2111; G06F 19/322; G06F 19/3443; G06F 19/325; G06F 19/326; G06F 19/345; G06F 21/6245; G06F 21/577; G06F 19/00; G06Q 10/087; G06Q 20/20; G06Q 20/202; G06Q 20/203; G06Q 30/0268; G06Q 30/0603; G06Q 40/00; G06Q 50/22; G06Q 50/24; G06Q 40/08; G06Q 10/10;
(Continued)

(56) References Cited

U.S. PATENT DOCUMENTS 6,636,833 B1 10/2003 Flitcroft
7,136,835 B1 11/2006 Flitcroft
(Continued)

OTHER PUBLICATIONS

Apriori algorithm, downloaded from http://en.wikipedia.org/wiki/Apriori_algorithm on Aug. 26, 2013, pp. 1-5.
(Continued)

*Primary Examiner* — Li Wu Chang
(74) *Attorney, Agent, or Firm* — Otterstedt, Wallace & Kammer, LLP

(57) ABSTRACT

Health-related data is accessed; as is a database of payment card transaction data. At least a portion of the health-related data is linked to at least a portion of the payment card transaction data to obtain linked data. Statistical analysis is carried out on the linked data, and the results of the statistical analysis are made available to at least one appropriate party. Privacy is protected, for example, via an opt-in approach or through data aggregation.

6 Claims, 14 Drawing Sheets

(58) Field of Classification Search
CPC ... G06Q 40/12; H04L 63/1483; H04L 67/306; G16H 50/80; G16H 50/30
See application file for complete search history.

(56) References Cited

U.S. PATENT DOCUMENTS

| | | | |
|---|---|---|---|
| 7,403,922 B1 | 7/2008 | Lewis | |
| 7,905,399 B2 | 3/2011 | Barnes | |
| 8,306,846 B2 | 11/2012 | Tavares | |
| 8,768,736 B1 | 7/2014 | Chapman | |
| 10,185,809 B1* | 1/2019 | Zhou | G06Q 30/0205 |
| 2003/0126094 A1* | 7/2003 | Fisher | G06Q 20/26 705/75 |
| 2007/0005396 A1 | 1/2007 | Lee | |
| 2007/0106582 A1 | 5/2007 | Baker | |
| 2007/0118399 A1 | 5/2007 | Avinash | |
| 2009/0254971 A1 | 10/2009 | Herz | |
| 2011/0145080 A1 | 6/2011 | Green | |
| 2012/0036013 A1* | 2/2012 | Neuhaus | G06Q 30/02 705/14.53 |
| 2013/0024242 A1 | 1/2013 | Villars | |
| 2013/0231976 A1 | 9/2013 | Tavares | |
| 2013/0318027 A1 | 11/2013 | Almogy | |
| 2014/0040134 A1* | 2/2014 | Ciurea | G06Q 20/383 705/44 |
| 2014/0180767 A1 | 6/2014 | Villars | |
| 2015/0169839 A1 | 6/2015 | Zhang | |
| 2015/0269346 A1 | 9/2015 | Lee | |

OTHER PUBLICATIONS

Association rule learning, downloaded from http://en.wikipedia.org/wiki/Association_rule_learning on Dec. 18, 2013, pp. 1-10.
Binomial regression, downloaded from http://en.wikipedia.org/wiki/Binomial_regression on Dec. 18, 2013, pp. 1-5.
Cluster analysis, downloaded from http://en.wikipedia.org/wiki/Cluster_analysis on Dec. 18, 2013, pp. 1-19.
Correlation and dependence, downloaded from http://en.wikipedia.org/wiki/Correlation on Aug. 26, 2013, pp. 1-9.
Decision tree learning, downloaded from http://en.wikipedia.org/wiki/Decision_tree_learning on Aug. 26, 2013, pp. 1-7.
K-means clustering, downloaded from http://en.wikipedia.org/wiki/K-means on Aug. 26, 2013, pp. 1-9.
Linear discriminant analysis, downloaded from http://en.wikipedia.org/wiki/Linear_discriminant_analysis on Aug. 26, 2013, pp. 1-6.
Logistic regression, downloaded from http://en.wikipedia.org/wiki/Logistic_regression on Aug. 26, 2013, pp. 1-15.
Longitudinal study, downloaded from http://en.wikipedia.org/wiki/Longitudinal_study on Dec. 18, 2013, pp. 1-3.
Negative binomial distribution, downloaded from http://en.wikipedia.org/wiki/Negative_binomial_distribution on Dec. 18, 2013, pp. 1-11.
Principal component analysis, downloaded from http://en.wikipedia.org/wiki/Principal_component_analysis on Aug. 26, 2013, pp. 1-13.
Python (programming language), downloaded from http://en.wikipedia.org/wiki/Python_(programming_language) on Nov. 30, 2013, pp. 1-19.
R (programming language), downloaded from http://en.wikipedia.org/wiki/R_(programming_language) on Nov. 30, 2013, pp. 1-11.
Regression analysis, downloaded from hftp://en.wikipedia.org/wiki/Regression_analysis on Aug. 26, 2013, pp. 1-7.
SAS (software), downloaded from http://en.wikipedia.org/wiki/SAS_(software) on Nov. 30, 2013, pp. 1-5.
SAS language, downloaded from http://en.wikipedia.org/wiki/SAS_language on Nov. 30, 2013, pp. 1-2.
Stratified sampling, downloaded from http://en.wikipedia.org/wiki/Stratified_sampling on Dec. 18, 2013, pp. 1-4.
Supervised learning, downloaded from http://en.wikipedia.org/wiki/Supervised_learning on Dec. 18, 2013, pp. 1-8.
Time series, downloaded from http://en.wikipedia.org/wiki/Time_series on Aug. 26, 2013, pp. 1-10.
Unsupervised learning, downloaded from http://en.wikipedia.org/wiki/Unsupervised_learning on Dec. 18, 2013, pp. 1-2.
Rakesh Agrawal et al, "Fast Algorithms for Mining Association Rules" Proceedings of the 20th VLDB Conference Santiago, Chile. 1994, pp. 1-13.
Data mining, Downloaded From http://en.wikipedia.org/wiki/Data_mining on Jan. 17, 2014, pp. 1-20.
IBM Netezza Data Warehouse Appliances, downloaded from http://www-01.ibm.com/software/data/netezza/ Jan. 17, 2014 p. 1.
Drentea et al. "Over the limit: the association among health, race and Debt", Social Science & Medicine 50, 2000, pp. 517-529.
Yildiz et al. "Integrated Approach for Privacy Preserving Itemset Mining" Intelligent Control and Innovative Computing, 2012, pp. 247-260.

\* cited by examiner

PRIVACY-COMPLIANT ANALYSIS OF HEALTH BY TRANSACTION DATA

CROSS REFERENCE TO RELATED APPLICATIONS

This patent application is a continuation of U.S. patent application Ser. No. 14/133,081, filed Dec. 18, 2013, entitled PRIVACY-COMPLIANT ANALYSIS OF HEALTH BY TRANSACTION DATA. The complete disclosure of the aforementioned U.S. patent application Ser. No. 14/133,081 is expressly incorporated herein by reference in its entirety for all purposes.

FIELD OF THE DISCLOSURE

The present disclosure relates generally to the electronic and computer arts, and, more particularly, to apparatus and methods for analysis of electronic payment data.

BACKGROUND OF THE DISCLOSURE

The use of payment cards, such as credit cards, debit cards, and pre-paid cards, has become ubiquitous. Most payment card accounts have one or more associated physical cards; however, the use of non-traditional payment devices, such as appropriately-configured "smart" cellular telephones, is increasing. A wealth of transaction data is available based on the use of payment card accounts.

Statistical analysis involves the collection, organization, analysis, interpretation and presentation of data. Machine learning concerns the construction and study of systems that can learn from data.

SUMMARY OF THE DISCLOSURE

Principles of the disclosure provide techniques for privacy-compliant analysis of health by transaction data. In one aspect, an exemplary method includes the steps of accessing health-related data; accessing a database of payment card transaction data; linking at least a portion of the health-related data to at least a portion of the payment card transaction data to obtain linked data; carrying out statistical analysis on the linked data; and making results of the statistical analysis available to at least one appropriate party.

Aspects of the disclosure contemplate the method(s) performed by one or more entities herein, as well as facilitating one or more method steps by the same or different entities. As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the disclosure or elements thereof can be implemented in the form of a computer program product including a tangible computer readable recordable storage medium with computer usable program code for performing the method steps indicated stored thereon in a non-transitory manner. Furthermore, one or more embodiments of the disclosure or elements thereof can be implemented in the form of a system (or apparatus) including a memory and at least one processor that is coupled to the memory and operative to perform exemplary method steps. Yet further, in another aspect, one or more embodiments of the disclosure or elements thereof can be implemented in the form of means for carrying out one or more of the method steps described herein; the means can include (i) specialized hardware module(s), (ii) software module(s) stored in a non-transitory manner in a tangible computer-readable recordable storage medium (or multiple such media) and implemented on a hardware processor, or (iii) a combination of (i) and (ii); any of (i)-(iii) implement the specific techniques set forth herein.

One or more embodiments of the disclosure can provide substantial beneficial technical effects; for example, assisting governmental or other authorities in quickly identifying epidemiological risks.

These and other features and advantages of the present disclosure will become apparent from the following detailed description of illustrative embodiments thereof, which is to be read in connection with the accompanying drawings.

DETAILED DESCRIPTION OF PREFERRED EMBODIMENTS

Payment Devices and Associated Payment Processing Networks

Figure 1:
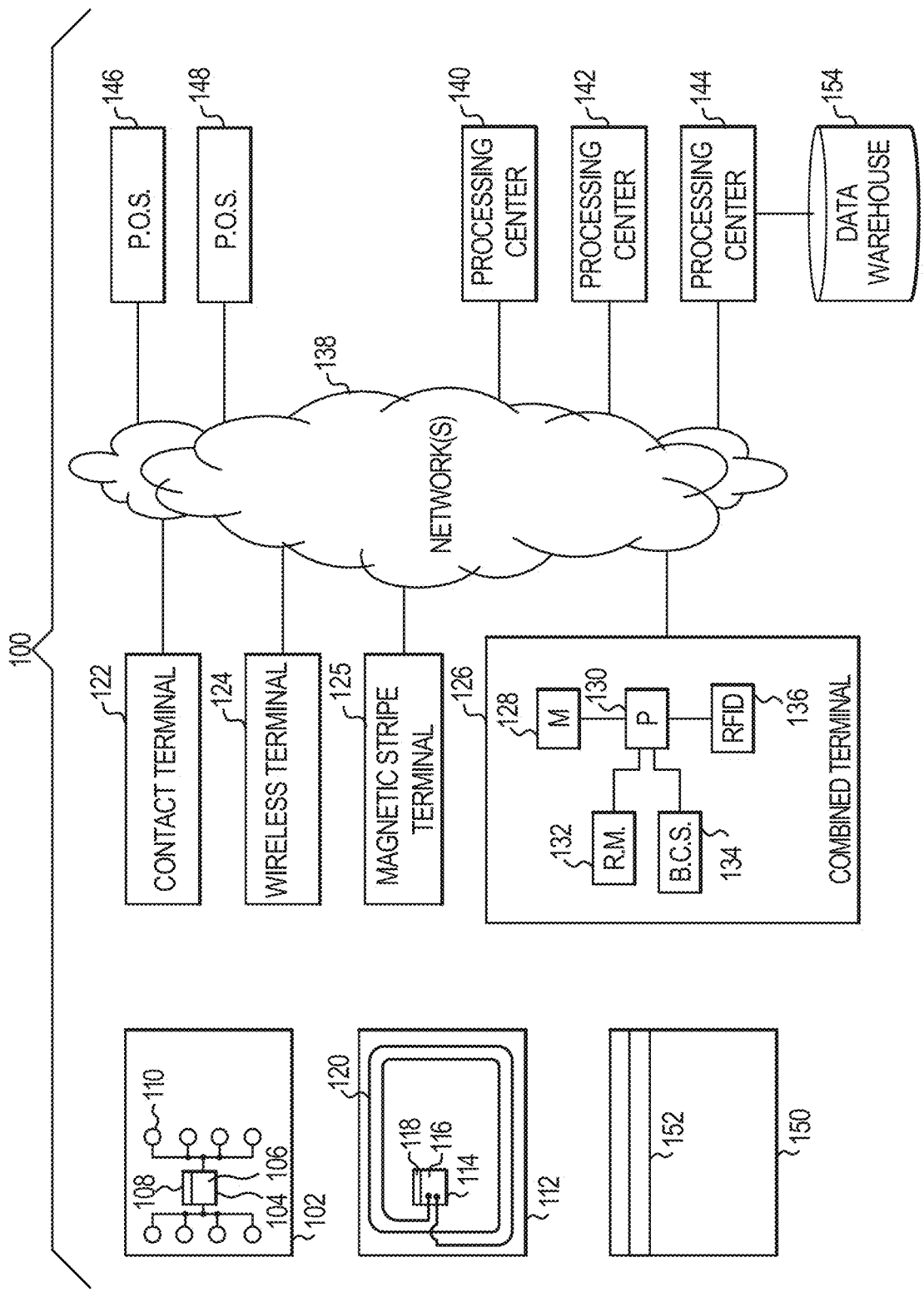
FIG. 1 shows an example of a system and various components thereof that can implement techniques of the disclosure.

Attention should now be given to FIG. 1, which depicts an exemplary embodiment of a system 100, according to an aspect of the disclosure, and including various possible components of the system. System 100 can include one or more different types of portable payment devices. For example, one such device can be a contact device such as card 102. Card 102 can include an integrated circuit (IC) chip 104 having a processor portion 106 and a memory portion 108. A plurality of electrical contacts 110 can be provided for communication purposes. In addition to or instead of card 102, system 100 can also be designed to work with a contactless device such as card 112. Card 112 can include an IC chip 114 having a processor portion 116 and a memory portion 118. An antenna 120 can be provided for contactless communication, such as, for example, using radio frequency (RF) electromagnetic waves. An oscillator or oscillators, and/or additional appropriate circuitry for one or more of modulation, demodulation, downconversion, and the like can be provided. Note that cards 102, 112 are exemplary of a variety of devices that can be employed. The system 100 per se may function with other types of devices in lieu of or in addition to "smart" or "chip" cards 102, 112; for example, a conventional card 150 having a magnetic stripe 152. Furthermore, an appropriately configured mobile device (e.g., "smart" cellular telephone handset, tablet, personal digital assistant (PDA), and the like) can be used to carry out contactless payments in some instances.

The ICs 104, 114 can contain processing units 106, 116 and memory units 108, 118. Preferably, the ICs 104, 114 can also include one or more of control logic, a timer, and input/output ports. Such elements are well known in the IC art and are not separately illustrated. One or both of the ICs 104, 114 can also include a co-processor, again, well-known and not separately illustrated. The control logic can provide, in conjunction with processing units 106, 116, the control necessary to handle communications between memory unit 108, 118 and the input/output ports. The timer can provide a timing reference signal from processing units 106, 116 and the control logic. The co-processor could provide the ability to perform complex computations in real time, such as those required by cryptographic algorithms.

The memory portions or units 108, 118 may include different types of memory, such as volatile and non-volatile memory and read-only and programmable memory. The memory units can store transaction card data such as, e.g., a user's primary account number ("PAN") and/or personal identification number ("PIN"). The memory portions of units 108, 118 can store the operating system of the cards 102, 112. The operating system loads and executes applications and provides file management or other basic card services to the applications. One operating system that can be used to implement some aspects or embodiments of the present disclosure is the MULTOS® operating system licensed by MAOSCO Limited. (MAOSCO Limited, St. Andrews House, The Links, Kelvin Close, Birchwood, Warrington, WA3 7PB, United Kingdom) Alternatively, JAVA CARD™-based operating systems, based on JAVA CARD™ technology (licensed by Sun Microsystems, Inc., 4150 Network Circle, Santa Clara, Calif. 95054 USA), or proprietary operating systems available from a number of vendors, could be employed. Preferably, the operating system is stored in read-only memory ("ROM") within memory portion 108, 118. In an alternate embodiment, flash memory or other non-volatile and/or volatile types of memory may also be used in the memory units 108, 118.

In addition to the basic services provided by the operating system, memory portions 108, 118 may also include one or more applications. At present, one possible specification to which such applications may conform is the EMV interoperable payments specification set forth by EMVCo, LLC (901 Metro Center Boulevard, Mailstop M3-3D, Foster City, Calif., 94404, USA). It will be appreciated that applications can be configured in a variety of different ways.

The skilled artisan will also be familiar with the MasterCard® PayPass™ specifications, available under license from MasterCard International Incorporated of Purchase, N.Y., USA (trademarks of MasterCard International Incorporated of Purchase, N.Y., USA).

As noted, cards 102, 112 are examples of a variety of payment devices that can be employed. The primary function of the payment devices may not be payment, for example, they may be cellular phone handsets that implement appropriate techniques. Such devices could include cards having a conventional form factor, smaller or larger cards, cards of different shape, key fobs, personal digital assistants (PDAs), appropriately configured cell phone handsets, or indeed any device with the appropriate capabilities. In some cases, the cards, or other payment devices, can include body portions (e.g., laminated plastic layers of a payment card, case or cabinet of a PDA, chip packaging, and the like), memories 108, 118 associated with the body portions, and processors 106, 116 associated with the body portions and coupled to the memories. The memories 108, 118 can contain appropriate applications. The processors 106, 116 can be operative to execute one or more steps. The applications can be, for example, application identifiers (AIDs) linked to software code in the form of firmware plus data in a card memory such as an electrically erasable programmable read-only memory (EEPROM).

A number of different types of terminals can be employed with system 100. Such terminals can include a contact terminal 122 configured to interface with contact-type device 102, a wireless terminal 124 configured to interface with wireless device 112, a magnetic stripe terminal 125 configured to interface with a magnetic stripe device 150, or a combined terminal 126. Combined terminal 126 is designed to interface with any combination of devices 102, 112, 150. Some terminals can be contact terminals with plug-in contactless readers. Combined terminal 126 can include a memory 128, a processor portion 130, a reader module 132, and optionally an item interface module such as a bar code scanner 134 and/or a radio frequency identification (RFID) tag reader 136. Items 128, 132, 134, 136 can be coupled to the processor 130. Note that the principles of construction of terminal 126 are applicable to other types of terminals and are described in detail for illustrative purposes. Reader module 132 can, in general, be configured for contact communication with card or device 102, contactless communication with card or device 112, reading of magnetic stripe 152, or a combination of any two or more of the foregoing (different types of readers can be provided to interact with different types of cards e.g., contacted, magnetic stripe, or contactless). Terminals 122, 124, 125, 126 can be connected to one or more processing centers 140, 142, 144 via a computer network 138. Network 138 could include, for example, the Internet, or a proprietary network (e.g., a virtual private network (VPN) such as is described with respect to FIG. 2 below). More than one network could be employed to connect different elements of the system. For example, a local area network (LAN) could connect a terminal to a local server or other computer at a retail establishment or the like. A payment network could connect acquirers and issuers. Further details regarding one specific form of payment network will be provided below. Processing centers 140, 142, 144 can include, for example, a host computer of an issuer of a payment device.

Many different retail or other establishments, represented by points-of-sale 146, 148, can be connected to network 138. Different types of portable payment devices, terminals, or other elements or components can combine or "mix and match" one or more features depicted on the exemplary devices in FIG. 1.

Portable payment devices can facilitate transactions by a user with a terminal, such as 122, 124, 125, 126, of a system such as system 100. Such a device can include a processor, for example, the processing units 106, 116 discussed above. The device can also include a memory, such as memory portions 108, 118 discussed above, that is coupled to the processor. Further, the device can include a communications module that is coupled to the processor and configured to interface with a terminal such as one of the terminals 122, 124, 125, 126. The communications module can include, for example, the contacts 110 or antennas 120 together with appropriate circuitry (such as the aforementioned oscillator or oscillators and related circuitry) that permits interfacing with the terminals via contact or wireless communication. The processor of the apparatus can be operable to perform one or more steps of methods and techniques. The processor can perform such operations via hardware techniques, and/or under the influence of program instructions, such as an application, stored in one of the memory units.

The portable device can include a body portion. For example, this could be a laminated plastic body (as discussed above) in the case of "smart" or "chip" cards 102, 112, or the handset chassis and body in the case of a cellular telephone.

It will be appreciated that the terminals 122, 124, 125, 126 are examples of terminal apparatuses for interacting with a payment device of a holder. The apparatus can include a processor such as processor 130, a memory such as memory 128 that is coupled to the processor, and a communications module such as reader module 132 that is coupled to the processor and configured to interface with the portable apparatuses 102, 112, 150. The processor 130 can be operable to communicate with portable payment devices of a user via the reader module 132. The terminal apparatuses can function via hardware techniques in processor 130, or by program instructions stored in memory 128. Such logic could optionally be provided from a central location such as processing center 140 over network 138. The aforementioned bar code scanner 134 and/or RFID tag reader 136 can optionally be provided, and can be coupled to the processor, to gather attribute data, such as a product identification from a UPC code or RFID tag on a product to be purchased.

The above-described devices 102, 112 can be International Organization for Standardization (ISO) 7816-compliant contact cards or devices or NFC (Near Field Communications) or ISO 14443-compliant proximity cards or devices. In operation, card 112 can be touched or tapped on the wireless terminal 124 or reader module 132 (or an associated reader), which then contactlessly transmits the electronic data to the proximity IC chip in the card 112 or other wireless device.

One or more of the processing centers 140, 142, 144 can include a database such as a data warehouse 154.

In some cases, there can be payment card accounts that do not have physical cards or other physical payment devices associated therewith; for example, a customer can be provided with a PAN, expiration date, and security code, but no physical payment device, and use same, for example, for card-not-present telephone or internet transactions. Transaction data for such accounts is also pertinent in one or more embodiments.

Figure 2:
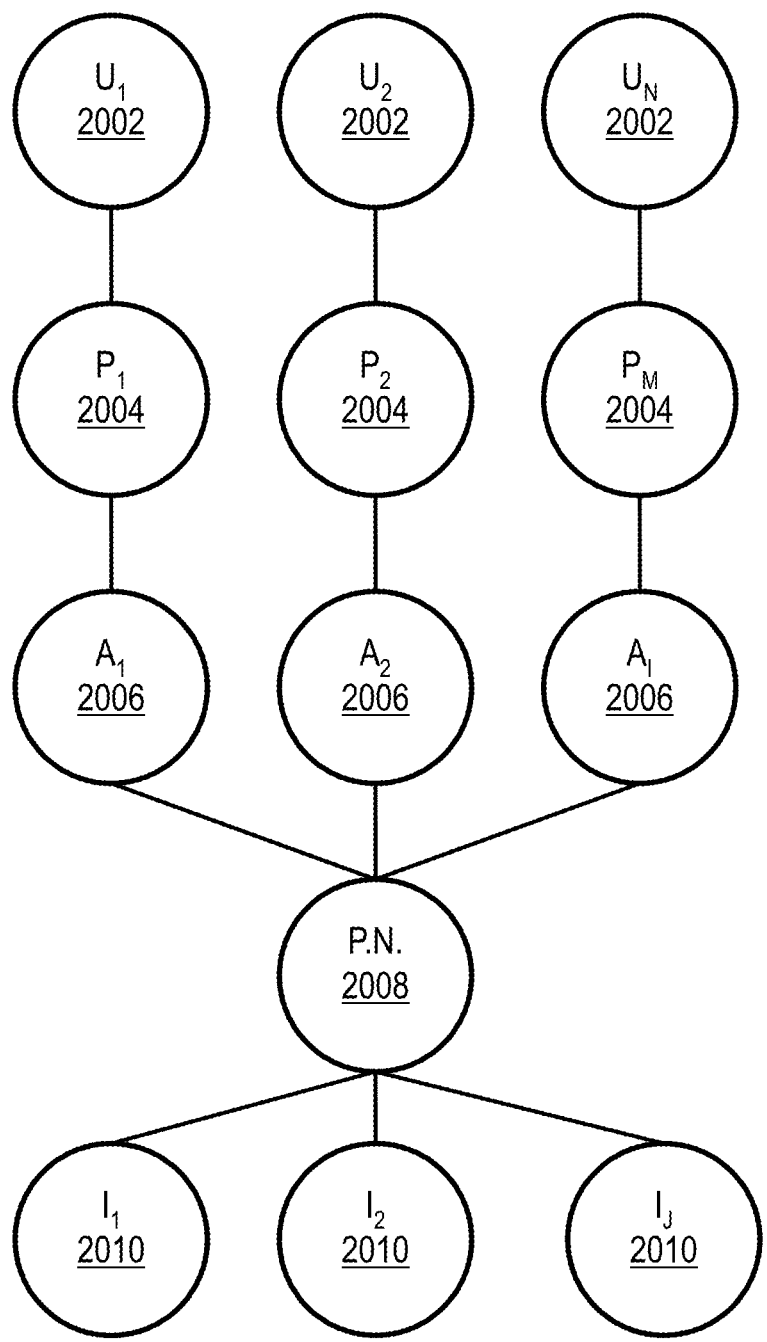
FIG. 2 depicts an exemplary inter-relationship between and among: (i) a payment network configured to facilitate transactions between multiple issuers and multiple acquirers, (ii) a plurality of users, (iii) a plurality of merchants, (iv) a plurality of acquirers, and (v) a plurality of issuers.

With reference to FIG. 2, an exemplary relationship among multiple entities is depicted. A number of different users (e.g., consumers) 2002, $U_1, U_2 \ldots U_N$, interact with a number of different merchants 2004, $P_1, P_2 \ldots P_M$. Merchants 2004 interact with a number of different acquirers 2006, $A_1, A_2 \ldots A_I$. Acquirers 2006 interact with a number of different issuers 2010, $I_1, I_2 \ldots I_J$, through, for example, a single operator of a payment network 2008 configured to facilitate transactions between multiple issuers and multiple acquirers; for example, MasterCard International Incorporated, operator of the BANKNET® network, or Visa International Service Association, operator of the VISANET® network. In general, N, M, I, and J are integers that can be equal or not equal.

During a conventional credit authorization process, the consumer 2002 pays for the purchase and the merchant 2004 submits the transaction to the acquirer (acquiring bank) 2006. The acquirer verifies the card number, the transaction type and the amount with the issuer 2010 and reserves that amount of the cardholder's credit limit for the merchant. At this point, the authorization request and response have been exchanged, typically in real time. Authorized transactions are stored in "batches," which are sent to the acquirer 2006. During subsequent clearing and settlement, the acquirer sends the batch transactions through the payment card network 2008, which debits the issuers 2010 for payment and credits the acquirer 2006. Once the acquirer 2006 has been paid, the acquirer 2006 pays the merchant 2004.

It will be appreciated that the payment card network 2008 shown in FIG. 2 is an example of a payment network configured to facilitate transactions between multiple issuers and multiple acquirers, which may be thought of as an "open" system. Some embodiments of the disclosure may be employed with other kinds of payment networks, for example, proprietary or closed payments networks with only a single issuer and acquirer, as long as the network provides a mechanism by which cards' prior transaction activity can be analyzed. Furthermore in this regard, FIG. 2 depicts a four party model, as will be known to the skilled artisan; the four parties are the consumer 2002, merchant 2004, acquirer 2006, and issuer 2010. However, at least some embodiments are also of use with three-party models, wherein the acquirer and issuer are the same entity.

Messages within a network such as network 138 and/or network 2008, may, in at least some instances, conform to the ISO Standard 8583, Financial transaction card originated messages—Interchange message specifications, which is the ISO standard for systems that exchange electronic transactions made by cardholders using payment cards. It should be noted that the skilled artisan will be familiar with the ISO 8583 standards. Nevertheless, out of an abundance of caution, the following documents are expressly incorporated herein by reference in their entirety for all purposes (published by ISO, Geneva, Switzerland, and available on the ISO web site):

ISO 8583 Part 1: Messages, data elements and code values (2003)

ISO 8583 Part 2: Application and registration procedures for Institution Identification Codes (IIC) (1998)

ISO 8583 Part 3: Maintenance procedures for messages, data elements and code values (2003)

ISO 8583:1993 (1993)

ISO 8583:1987 (1987)

As used herein, a "payment card network" is a communications network that uses payment card account numbers, such as primary account numbers (PANs), to authorize, and to facilitate clearing and settlement of, payment card transactions for credit, debit, stored value and/or prepaid card accounts. The card accounts have standardized payment card account numbers associated with them, which allow for efficient routing and clearing of transactions; for example, ISO standard account numbers such as ISO/IEC 7812-compliant account numbers. The card accounts and/or account numbers may or may not have physical cards or other physical payment devices associated with them. For example, in some instances, organizations have purchasing card accounts to which a payment card account number is assigned, used for making purchases for the organization, but there is no corresponding physical card. In other instances, "virtual" account numbers are employed; this is also known as PAN mapping. The PAN mapping process involves taking the original Primary Account Number (PAN) (which may or may not be associated with a physical card) and issuing a pseudo-PAN (or virtual card number) in its place. Commercially available PAN-mapping solutions include those available from Orbiscom Ltd., Block 1, Blackrock Business Park, Carysfort Avenue, Blackrock, Co. Dublin, Ireland (now part of MasterCard International Incorporated of Purchase, N.Y., USA); by way of example and not limitation, techniques of U.S. Pat. Nos. 6,636,833 and 7,136,835 of Flitcroft et al., the complete disclosures of both of which are expressly incorporated herein by reference in their entireties for all purposes.

Some payment card networks connect multiple issuers with multiple acquirers; others use a three party model. Some payment card networks use ISO 8583 messaging. Non-limiting examples of payment card networks that connect multiple issuers with multiple acquirers are the BANK-NET® network and the VISANET® network.

One or more embodiments employ transaction data, such as transaction data from payment card accounts, in predicting consumers' health status by analyzing their transaction patterns. The information collected, and the reports generated, can be used, for example, by health care providers to bring better services to their patients, by various organizations to make consumers aware of pertinent products and/or services, and the like. Embodiments are intended to be used in full compliance with all applicable laws, regulations, policies, and procedures protecting privacy rights.

When people make purchases, where they make such purchases, and what they purchase can provide significant information; in one or more embodiments, whether the people likely are in good health status. For example, frequent purchases in fast food restaurants would be highly correlated to potential risk of diabetes; frequent visits to tanning salons may be correlated to potential risk of skin health problems, and so on. However, one or more embodiments are not limited to such direct correlations. One or more embodiments use statistical analysis and/or machine learning algorithms to explore a transaction database, discussed further below, to reveal hidden and/or more complex connections. For example, a combination of a series of transaction patterns may be correlated to one or more health issues.

Figure 3:
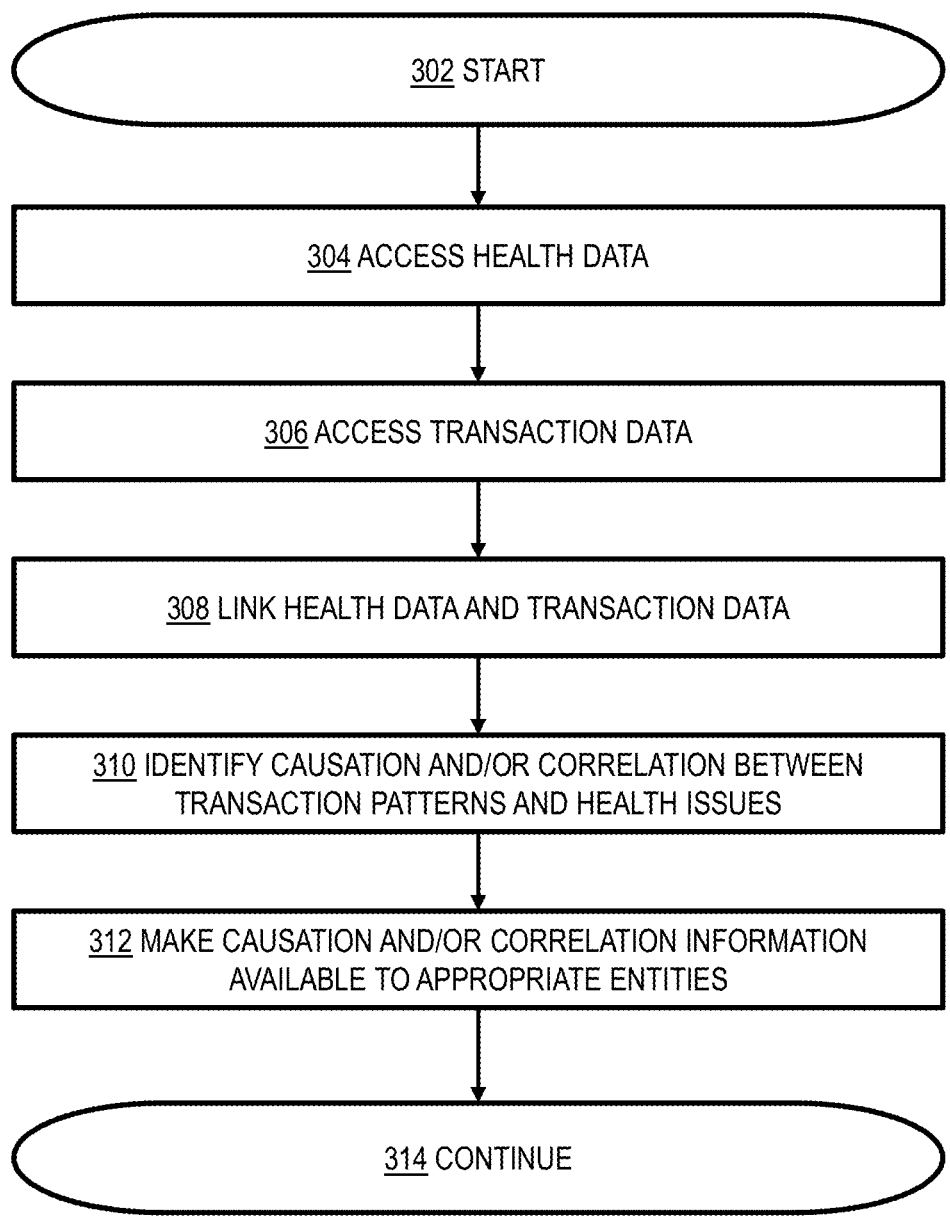
FIG. 3 is a flow chart of an exemplary method, in accordance with an aspect of the disclosure.

Refer now to the flow chart of FIG. 3, which begins at 302. In step 304, access health data; for example, by using a database module to query healthcare database 404. In step 306, access transaction data; for example, using the same, or a different, database module to query transaction database 402. Some instances include building one or more databases on which the analysis is to be conducted. In one or more embodiments, this does not necessarily require obtaining the health records from health providers or obtaining the transaction records from financial institutions. The data could come from various sources including, by way of example and not limitation, voluntary submission of one's own health records. In step 308, link one or more health issue indicators or health issue flags to transaction information for one or more individuals; for example, using a linkage module 408, discussed further below. As used herein, a health issue indicator or health issue flag is a variable from a modeling process, from which at least one attribute related to an individual's health can be inferred or predicted.

Various appropriate entities carry out one or more of these steps in one or more embodiments, subject to appropriate privacy protections; for example, health care providers who will need transaction information for one or more patients; financial institutions who need the health records for one or more patients; or a third party who can access both data sources (i.e., health and transaction) or is able to collect both types of data either from individuals or institutions. As discussed further below, some embodiments follow an opt-in model for privacy protection, and provide a tool for an individual who has opted-in to receive guidance about his or her health. Other embodiments follow an aggregated or anonymized model for privacy protection, and provide a mechanism for analysis of a broader population by public health authorities or the like.

In step 310, conduct statistical analysis and/or apply a suitable machine learning algorithm, for example, to find the potential causation and/or correlation between the transaction patterns and health issues; for example, using supervised learning module 410 and/or unsupervised learning module 412, discussed further below. Broadly, some instances employ supervised learning and some instances employ unsupervised learning. In step 312, make this information available to appropriate entities; for example, provide the information and service to health providers to increase their knowledge and improve services. Alternatively, merchants and marketers may use the system to find their best customers; of course, in accordance with all applicable privacy protection laws, rules, regulations, and procedures.

Processing continues at 314.

A variety of techniques can be employed to find causation and/or correlation between transaction patterns and health issues. As noted above, some instances employ supervised learning and some instances employ unsupervised learning. Non-limiting examples of the statistical analysis methods and/or machine learning algorithms that can be used include classification methods such as logistic regression, decision trees, and linear discriminant analysis; clustering methods such as principal component analysis (PCA) or K-Means; and association analysis methods such as Apriori algorithms, and the like. With regard to Apriori algorithms, the skilled artisan will be familiar with same, and given the teachings herein, will be able to adapt same to implement one or more embodiments—nevertheless, reference is made to Rakesh Agrawal and Ramakrishnan Srikant, Fast Algorithms for Mining Association Rules, Twentieth VLDB Conference, Santiago, Chile 1994. The Agrawal and Srikant reference is hereby expressly incorporated by reference herein in its entirety for all purposes. Further non-limiting exemplary details are discussed below.

While statistical analysis and machine learning algorithms have been applied to many different areas to uncover seemingly unrelated connections, heretofore, transaction data has not been used to analyze health issues. Advantageously, one or more embodiments implement health-related analysis of transaction data. Transaction data is a vast source of information, so that large number of health-related analyses can be carried out using such data. Further advantages of one or more embodiments are discussed below.

Figure 4:
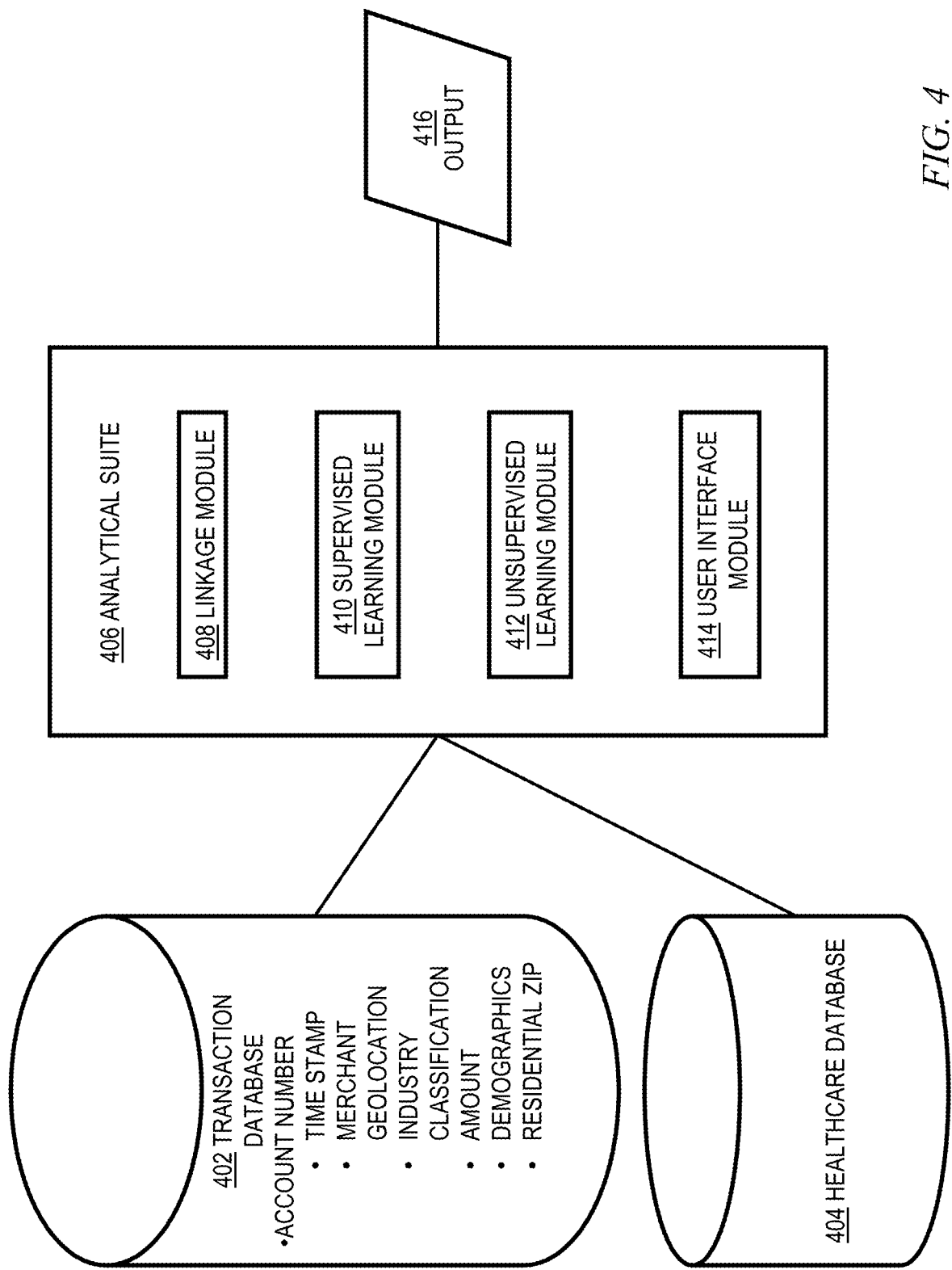
FIG. 4 is a block diagram of an exemplary system, in accordance with an aspect of the disclosure.

Referring now to the block diagram of FIG. 4, and particularly to the transaction database 402 therein, in one or more embodiments, payment fields that are of interest for modeling include timestamp, merchant geolocation, Industry Classification, transaction amount, and account number. Demographic data can also be appended in some instances. Optionally, generic merchant categories rather than specific merchant brand names are employed in one or more embodiments; for example, some persons might associate excessive fast food consumption with poor health habits so that identification by generic merchant categories rather than specific merchant brand names might be appropriate in some such circumstances. The cardholder's residential zip code can be inferred, in at least some cases, using methods disclosed in unpublished U.S. patent application Ser. No. 13/721,216 of first named inventor Curtis Villars, filed Dec. 20, 2012 and entitled METHOD AND SYSTEM FOR ASSIGNING SPENDING BEHAVIORS TO GEOGRAPHIC AREAS. The Villars reference is hereby expressly incorporated by reference herein in its entirety for all purposes and pertinent portions are reproduced below (figure and reference characters are changed as needed to avoid confusion with those of the present disclosure). Furthermore in this regard, residential zip code can be inferred by the centroid of transactions likely to be carried out near home; work zip code can be inferred by the centroid of transactions likely to be carried out near work. Zip code is a non-limiting example of a postal code or other similar geographic indicia.

In one or more embodiments, the data in transaction database 402 is then compared, correlated, and modeled with healthcare data in healthcare database 404 or the like, such as cancer prevalence data, heart attack prevalence, allergy prevalence data, or other healthcare data (such as databases available from the U.S. Federal Center for Disease Control or CDC).

Database 402 could be located, for example, within a payment processing network 2008.

One or more embodiments employ an analytical suite 406, to be discussed further below.

Two types of analyses are of interest in healthcare analysis in one or more embodiments; namely, supervised learning and unsupervised learning.

In one or more embodiments, the health data in the healthcare database 404 is linked with the payments data 402. For cardholder opt-in embodiments, this can be done, for example, by the cardholder, such as by having the cardholder identify which spend data (potentially across multiple payment card accounts) should be compared against health data that is uploaded by the cardholder. For aggregated embodiments, this linking can be done, for example, by travel destination, residence zip code, workplace zip code, demographic group, or some other factor. In one or more embodiments, this linkage is implemented by linkage module 408 of analytical suite 406. Furthermore in this regard, one or more embodiments use SQL to link or merge the databases 402, 404. The merchant's zip code can be used to determine where the merchant is located. Demographic information, optionally zip-code specific, can also be used. Thus, some embodiments link via zip code; that is to say, zip code is the "key." In the customer opt-in search embodiment, personal data from the customer can be linked via more detailed keys, such as an identification of the customer (e.g., PAN or other card account number from database 402 is linked to health account ID in healthcare database 404), which links his or her personal health information to his or her transaction information.

Supervised learning module 410 implements supervised learning aspects while unsupervised learning module 412 implements unsupervised learning aspects; non-limiting examples are provided below.

Two non-limiting exemplary embodiments will now be discussed. First, consider, for example, a cardholder opt-in embodiment. Suppose that a cardholder is ill, and doctors are having trouble diagnosing the cause. The doctors examine the cardholder's spend data for the past three years and determine that the cardholder vacationed in Arizona. Based on this information, the doctors conclude that the cardholder has 'Valley Fever' (a mold-related lung infection common in Arizona). In another example of a cardholder opt-in embodiment, a cardholder has been tracking his or her blood pressure and blood sugar levels for the past year, and wants to compare this information to his or her eating habits (conveniently recorded through his or her payment card).

The second non-limiting exemplary embodiment employs aggregated data to protect privacy. In one instance, a comparison is made of zip code level per capita spending on fast food (as defined by the cardholder's estimated residential zip code) and the number of heart surgeries per capita at hospitals in the zip code. This approach could also be further broken down by the kind of heart or other cardiovascular surgery (e.g., angioplasty) and/or could also be run at the county, state, or region level. Analysis could also be restricted to people over 35 or some other threshold age. In another instance, the aggregated group is everyone that has visited a specific restaurant, or traveled to a specific destination. The model permits comparison of the travel group to the residents of the destination, as well as the other travelers. This is believed to be advantageous, in one or more embodiments, because in known techniques, a person is compared to his or her local peers, and is therefore being diagnosed without regard to the region(s) where he or she traveled.

Thus, one or more embodiments employ transaction data in the transaction database 402 together with people's health records in the healthcare database 404 to predict one or more occurrences and/or search for correlations between the transaction data and health issues. One or more embodiments can be used to help individuals, government, institutions, and/or insurance companies. One approach is to use correlation time series; other approaches are discussed below. In some embodiments, one or more method steps are carried out or otherwise facilitated by an operator of a payment processing network 2008. Such an operator typically cannot use individual health transaction data without consent, and thus will employ anonymized (aggregated) data or else obtain consent in the aforementioned opt-in approach (e.g., a person voluntarily submits his or her own health information and the entity will match it to that person's transaction information, with his or her consent). Furthermore in this regard, all embodiments should comply fully with applicable laws, rules, regulations, policies and procedures designed to protect the security and privacy of health data (for example, in the U.S., The Health Insurance Portability and Accountability Act of 1996 (HIPAA; Pub.L. 104-191, 110 Stat. 1936, enacted Aug. 21, 1996)).

It is worth mentioning that health care records in healthcare database 404 and transactions in transaction database 402 are two conceptually different things. The transaction database 402 includes data on many different transactions, which, in general, may be with entities that are not doctors, pharmacies, or other health care providers (e.g., gasoline purchases, grocery purchases, utility bill payment, and so on), and may also be with entities that are doctors, pharmacies, or other health care providers. In some cases, where permitted by applicable laws, rules, regulations, and procedures, data in transaction database 402 from healthcare-related transactions can be used to populate healthcare database 404.

As noted, fields of interest in transaction database 402 include, for example, time, merchant location, industry classification, amount, optionally demographics, and so on. More, fewer, or different fields can be used in other embodiments. Furthermore with regard to the opt-in approach, health care records supplied by an individual are linked to his or her day-to-day card transactions. For example, does he or she buy running shoes or fast food thick shakes? This data is stored in a transaction database 402 in association with a person's card account number (PAN). The person is solicited and affirmatively opts in after full disclosure. The cardholder supplies the health information, for example, by submitting it personally (e.g., via user interface module 414) or signing a release which allows the doctor to supply same. This aspect provides, for example, a forecasting engine. For example, this aspect can provide a tool for a health conscious person; he or she opts in, answers some questions, and then correlates the answers with transaction information; e.g., frequent fast food visits.

Furthermore with regard to the approach employing aggregated or privatized data, in one or more embodiments, this aspect uses aggregated healthcare transaction information. Such information can be obtained, for example, from hospitals, pharmacies, by leveraging system demographic data from government or other public web sites, and so on. This aspect can be used, for example, to help public health authorities generally understand the state of the population's health in a geographic region or even a whole country.

Thus, non-limiting exemplary embodiments include "cardholder opt-in" and "aggregated data." Opt-in and aggregated data are two non-limiting examples of privacy-compliant data collection. Many different things can be done with the collected data.

As noted, some embodiments employ "supervised learning" and some employ "unsupervised learning." Some non-limiting examples follow.

Supervised learning: In supervised learning, the targets are given. Some embodiments employing supervised learning utilize stratified sampling combined with logistic regression, and negative binomial regression. These techniques can be used for opt-in or aggregated data cases. Many other classification methods can be used. However, stratified sampling combined with logistic regression, and negative binomial regression, are believed to be advantageous in one or more embodiments. In particular, for both opt-in and aggregated data cases, in most instances, the target population is quite small compared to the whole population, say (by way of example and not limitation) only 0.01% of the people have a certain disease and it is desired to know the relation to the transaction patterns of these diseased people. Common classification methods such as logistic regression or decision trees without stratification will typically yield poor results in such cases because the target is so unbalanced.

Some supervised learning embodiments employing supervised learning utilize a longitudinal analysis, time series, mixed model approach. Longitudinal analysis is one kind of repeated measurement, which fits the scenario of transaction data and health data. For example, a cardholder has been tracking his or her blood pressure and blood sugar levels for the past year, and wants to compare this information to his or her eating habits (conveniently recorded through his or her payment card).

Unsupervised learning: In supervised learning, the targets are not given. Some embodiments employing unsupervised learning utilize clustering. Clustering is one kind of unsupervised learning, and it can be applied in both opt-in and aggregated data cases. In some cases, it is used in opt-in approaches wherein specific health issues are not being targeted and the customer(s) are simply broken down into different buying segments (such as a nutrition shopper, alcohol shopper, cigarettes shopper) or life style segments (such as traveler, luxury shopper, budget, single, family-focused). These segments share their own similarities. This can be helpful in a number of ways; for example, it can be used by health professionals to categorize the customer to certain segments, and in the next step, useful analysis can be done based on this categorization and more specific supervised modeling models can be built on each health group, given targets, instead of building on the whole population. It is worth noting that clustering is actually one way of aggregation, but learned by the algorithms themselves.

Another kind of unsupervised learning is association rule learning, and Apriori learning is one of the most common types of association rule learning. It can be used, for example, to study the relationship of indicators with transaction or demographic data (example: {sporting goods, men's apparel}=>{gender}) (to fill in missing variables) or within targeted health issues (ex: {diabetes, high blood pressure}=>{heart disease}) (to predict), wherein the parameter after the "=>" symbol is implied by the parameters before the "=>" symbol.

Thus, advantageously, one or more embodiments:
  employ opt-in and/or aggregated data to build the foundation of data analysis for transaction data, in a privacy-compliant manner;
  provide several statistical learning methods (supervised and unsupervised) that help study and obtain insight with respect to transaction data and health data;
  provide a framework for analyzing transactional and health data, including collecting the data, deciding between supervised or unsupervised approaches, and selecting a suitable method.

As noted above, some embodiments employ "supervised learning" and some employ "unsupervised learning." In another aspect, in some instances, analytical techniques include, for example, correlation analysis and time series analysis. It is to be emphasized that these are non-limiting examples. In correlation analysis, two events overlap and/or coincide; in time series analysis, also known as longitudinal analysis, one event usually precedes another.

Recapitulation

Given the discussion thus far, it will be appreciated that, in general terms, an exemplary method, according to an aspect of the disclosure, includes the step 304 of accessing health-related data. This step can be carried out, for example, using a database module to query healthcare database 404. A further step 306 includes accessing a database of payment card transaction data; for example, using the same, or a different, database module to query transaction database 402. An even further step 308 includes linking at least a portion of the health-related data to at least a portion of the payment card transaction data to obtain linked data. This step can be carried out, for example, using a linkage module 408. Another step 310 includes carrying out statistical analysis on the linked data; for example, using supervised learning module 410 and/or unsupervised learning module 412. Yet another step 312 includes making results of the statistical analysis available to at least one appropriate party. This step can be carried out, for example, using user interface module 414 to produce output 416.

In an opt-in approach, further steps include obtaining consent from a holder of at least one payment card, for which card records are included in the payment card transaction data in transaction database 402; and obtaining, from the holder, an identification of at least one primary account number for the at least one payment card. The consent can be explicit, or in some cases, can be implicit, e.g., the cardholder voluntarily provides his or her PAN in the obtaining step after full disclosure. In this approach, the linking includes linking the health-related data to that portion of the payment card transaction data associated with the at least one primary account number; and, in the step of making the results available, the at least one appropriate party is the holder.

In some opt-in cases, the accessing of the health-related data includes obtaining the health-related data as input from the holder.

In some opt-in cases, the accessing of the health-related data includes obtaining the health-related data from a health care provider in response to a release from the holder.

In an aggregated approach, the health-related data in healthcare database 404 includes aggregated data, and the linking includes linking via at least one of a geographic and a demographic basis.

As noted, in some cases, the step of carrying out the statistical analysis on the linked data includes employing a supervised learning approach. In some cases, the supervised learning approach includes applying stratified sampling combined with logistic regression, and negative binomial regression. In some cases, the supervised learning approach includes applying longitudinal analysis.

As also noted, in some cases, the step of carrying out the statistical analysis on the linked data includes employing an unsupervised learning approach. In some cases, the unsupervised learning approach includes applying clustering. In some cases, the unsupervised learning approach includes applying association rule learning. In some cases, the applying of the association rule learning includes applying Apriori learning.

Note that, in general, consumer-related health care-related factors can include, by way of example and not limitation, travel, hobbies, food, drink, exercise, and/or participation in outdoor sports.

In some cases, in step 312, the results include an epidemiological predictor (broadly understood to include correlation, prediction, and causation). For example, in some cases, the epidemiological predictor includes a correlation or prediction regarding visiting a certain geographic location and incidence of a certain disease (see, e.g., 'Valley Fever' example above). In another non-limiting example, the epidemiological predictor includes at least one of a correlation and a prediction regarding patronizing a certain type of merchant and incidence of a certain disease (see, e.g., fast food examples above).

As noted, in some cases, an exemplary apparatus includes means for carrying the method steps described herein. Means for accessing health-related data can include a healthcare database module executing on at least one hardware processor. The specific algorithm includes, for example, the specific queries set forth herein. Means for accessing a database of payment card transaction data include a transaction database module executing on at least one hardware processor. The specific algorithm includes, for example, the specific queries set forth herein.

Means for linking at least a portion of the health-related data to at least a portion of the payment card transaction data to obtain linked data include a linkage module executing on at least one hardware processor. As noted above one or more embodiments use SQL to link or merge the databases 402, 404. SQL or Structured Query Language is a special-purpose programming language designed for managing data held in a relational database management system (RDMS). SQL and RDMS are non-limiting examples of query techniques and database management systems, respectively. Regarding the specific algorithms for linkage, refer to the above discussions of linkage with merchant's zip code; demographic information, optionally zip-code specific; and personal data from the customer linked via an identification of the customer (e.g., PAN or other card account number from transaction database 402 is linked to health account ID in healthcare database 404).

Means for carrying out statistical analysis on the linked data include a supervised learning module and/or an unsupervised learning module executing on at least one hardware processor. Regarding the specific algorithms, see above discussions of stratified sampling, longitudinal analysis, clustering, and association rule learning such as Apriori methods.

Means for making results of the statistical analysis available to at least one appropriate party include a user interface module, optionally producing output 416. The module can include, in some cases, an API when one or more techniques disclosed herein are offered as a service to a third party who accesses the API. In another aspect, the module can include a graphical user interface (GUI), such as that formed by a server serving out hypertext markup language (HTML) code to a browser of a user.

System and Article of Manufacture Details

Embodiments of the disclosure can employ hardware and/or hardware and software aspects. Software includes, but is not limited to, firmware, resident software, microcode, etc. Software might be employed, for example, in connection with one or more of analytical suite 406 and its related modules; a terminal 122, 124, 125, 126; a reader module 132; a host, server, and/or processing center 140, 142, 144 (optionally with data warehouse 154) of a merchant, issuer, acquirer, processor, or operator of a network 2008, operating according to a payment system standard (and/or specification); and the like. Firmware might be employed, for example, in connection with payment devices such as cards 102, 112, as well as reader module 132.

Figure 5:
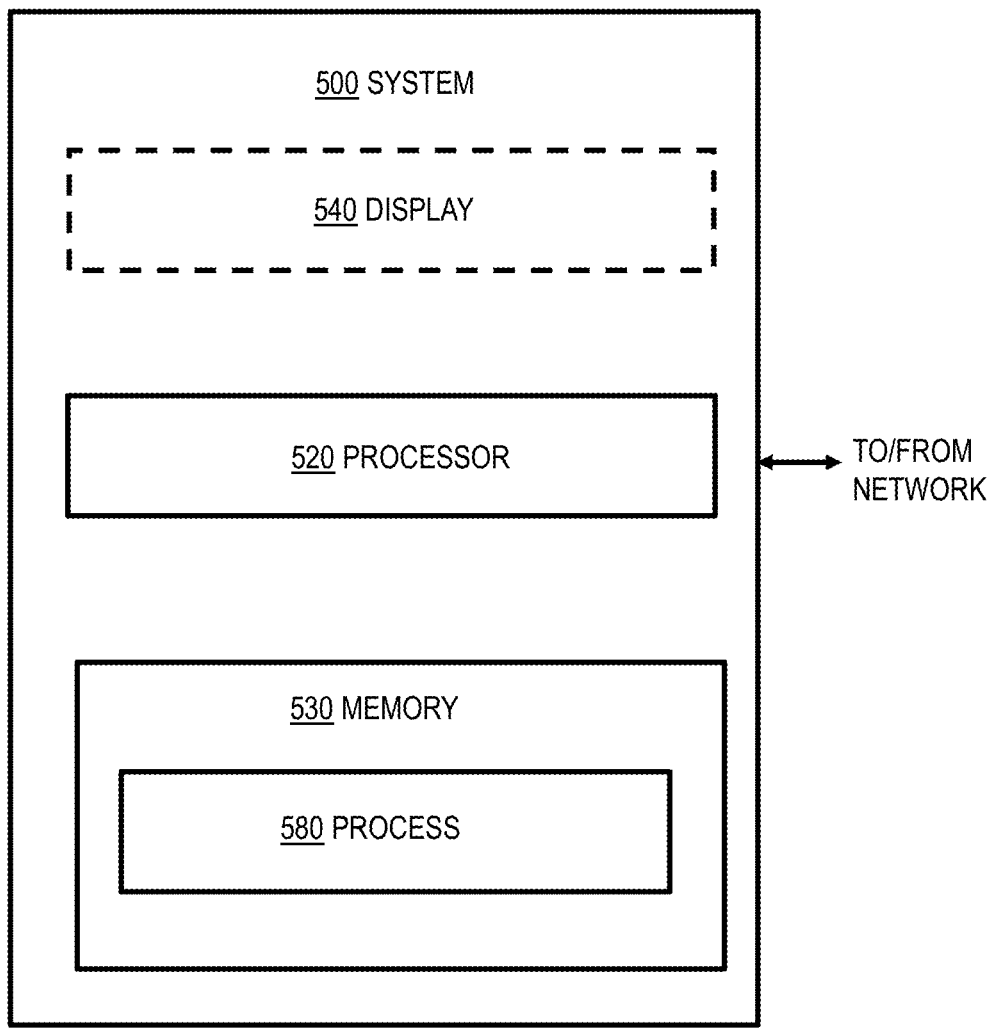
FIG. 5 is a block diagram of an exemplary computer system useful in one or more embodiments of the disclosure.

FIG. 5 is a block diagram of a system 500 that can implement part or all of one or more aspects or processes of the disclosure. As shown in FIG. 5, memory 530 configures the processor 520 (which could correspond, e.g., to processor portions 106, 116, 130; a processor of a terminal or a reader module 132; processors of remote hosts in centers 140, 142, 144; processors of hosts and/or servers implementing various functionality such as that of analytical suite 406; and the like); to implement one or more aspects of the methods, steps, and functions disclosed herein (collectively, shown as process 580 in FIG. 5). Different method steps can be performed by different processors. The memory 530 could be distributed or local and the processor 520 could be distributed or singular. The memory 530 could be implemented as an electrical, magnetic or optical memory, or any combination of these or other types of storage devices (including memory portions as described above with respect to cards 102, 112). It should be noted that if distributed processors are employed, each distributed processor that makes up processor 520 generally contains its own addressable memory space. It should also be noted that some or all of computer system 500 can be incorporated into an application-specific or general-use integrated circuit. For example, one or more method steps could be implemented in hardware in an ASIC rather than using firmware. Display 540 is representative of a variety of possible input/output devices (e.g., displays, printers, keyboards, mice, touch pads, and so on).

As is known in the art, part or all of one or more aspects of the methods and apparatus discussed herein may be distributed as an article of manufacture that itself comprises a tangible computer readable recordable storage medium having computer readable code means embodied thereon. The computer readable program code means is operable, in conjunction with a computer system, to carry out all or some of the steps to perform the methods or create the apparatuses discussed herein. A computer-usable medium may, in general, be a recordable medium (e.g., floppy disks, hard drives, compact disks, EEPROMs, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk. The medium can be distributed on multiple physical devices (or over multiple networks). For example, one device could be a physical memory media associated with a terminal and another device could be a physical memory media associated with a processing center. As used herein, a tangible computer-readable recordable storage medium is defined to encompass a recordable medium (non-transitory storage), examples of which are set forth above, but does not encompass a transmission medium or disembodied signal.

The computer systems and servers described herein each contain a memory that will configure associated processors to implement the methods, steps, and functions disclosed herein. Such methods, steps, and functions can be carried out, by way of example and not limitation, by processing capability on one, some, or all of elements 122, 124, 125, 126, 140, 142, 144, 2004, 2006, 2008, 2010; on a computer implementing analytical suite 406 interacting with databases 402, 404; and the like. The memories could be distributed or local and the processors could be distributed or singular. The memories could be implemented as an electrical, magnetic or optical memory, or any combination of these or other types of storage devices. Moreover, the term "memory" should be construed broadly enough to encompass any information able to be read from or written to an address in the addressable space accessed by an associated processor. With this definition, information on a network is still within a memory because the associated processor can retrieve the information from the network.

Thus, elements of one or more embodiments of the disclosure, such as, for example, 122, 124, 125, 126, 140, 142, 144, 2004, 2006, 2008, 2010; a computer implementing suite 406 interacting with databases 402, 404, and the like, can make use of computer technology with appropriate instructions to implement method steps described herein. Some aspects can be implemented, for example, using one or more servers which include a memory and at least one processor coupled to the memory. The memory could load appropriate software. The processor can be operative to perform one or more method steps described herein or otherwise facilitate their performance.

Accordingly, it will be appreciated that one or more embodiments of the disclosure can include a computer program comprising computer program code means adapted to perform one or all of the steps of any methods or claims set forth herein when such program is run on a computer, and that such program may be embodied on a computer readable medium. Further, one or more embodiments of the present disclosure can include a computer comprising code adapted to cause the computer to carry out one or more steps of methods or claims set forth herein, together with one or more apparatus elements or features as depicted and described herein.

As used herein, including the claims, a "server" includes a physical data processing system (for example, system 500 as shown in FIG. 5) running a server program. It will be understood that such a physical server may or may not include a display, keyboard, or other input/output components. A "host" includes a physical data processing system (for example, system 500 as shown in FIG. 5) running an appropriate program.

Furthermore, it should be noted that any of the methods described herein can include an additional step of providing a system comprising distinct software modules embodied on one or more tangible computer readable storage media. All the modules (or any subset thereof) can be on the same medium, or each can be on a different medium, for example. The modules can include any or all of the components shown in the figures. In one or more embodiments, the modules include a linkage module 408, a supervised learning module 410, an unsupervised learning module 412, a user interface module 414; and one or more database modules implementing elements 402 and/or 404 and optionally, output 416. The method steps can then be carried out using the distinct software modules of the system, as described above, executing on the one or more hardware processors. Further, a computer program product can include a tangible computer-readable recordable storage medium with code adapted to be executed to carry out one or more method steps described herein, including the provision of the system with the distinct software modules.

Computers discussed herein can be interconnected, for example, by one or more of network 138, 2008, another virtual private network (VPN), the Internet, a local area and/or wide area network (LAN and/or WAN), via an EDI layer, and so on. Note that element 2008 represents both the network and its operator. The computers can be programmed, for example, in compiled, interpreted, object-oriented, assembly, and/or machine languages, for example, one or more of C, C++, Java, Visual Basic, COBOL, Assembler, and the like (an exemplary and non-limiting list), and can also make use of, for example, Extensible Markup Language (XML), known application programs such as relational database applications, spreadsheets, and the like. Some embodiments make use of SAS software, the Python programming language, and/or the R software environment for statistical computing and graphics. The computers can be programmed to implement the logic depicted in the figures. In some instances, messaging and the like may be in accordance with ISO Specification 5583 Financial transaction card originated messages—Interchange message specifications and/or the ISO 20022 or UNIFI Standard for Financial Services Messaging, also incorporated herein by reference in its entirety for all purposes.

Although illustrative embodiments have been described herein with reference to the accompanying drawings, it is to be understood that those precise embodiments are non-limiting, and that various other changes and modifications may be made by one skilled in the art without departing from the scope or spirit of the disclosure.

Reproduction of Certain Portions of U.S. patent application Ser. No. 13/721,216 of First Named Inventor Curtis Villars, Filed Dec. 20, 2012 and Entitled METHOD AND SYSTEM FOR ASSIGNING SPENDING BEHAVIORS TO GEOGRAPHIC AREAS The present disclosure provides a description of a system and method for assigning spending behaviors to geographic areas.

A method for identifying spending behaviors in a geographic area includes: storing, in a database, a plurality of geographic centroids, wherein each geographic centroid corresponds to a centroid of a predefined geographic area; receiving, by a receiving device, a plurality of financial transactions involving each consumer of a plurality of consumers; identifying, by a processing device, a geographic location of each financial transaction of the plurality of financial transactions; calculating, for each consumer of the plurality of consumers, a purchase centroid of the financial transactions involving the consumer based on a centroid of the identified geographic location of each of the financial transactions involving the consumer; analyzing, for each consumer, spending behaviors based on the financial transactions involving the consumer; associating the analyzed spending behavior for each consumer with the corresponding purchase centroid; associating, in the database, the analyzed spending behaviors for each purchase centroid with a predetermined number of geographic centroids based on the distance from the purchase centroid to each of the predetermined number of geographic centroids; and aggregating, in the database, each of the spending behaviors associated with each geographic centroid of the plurality of geographic centroids such that each corresponding geographic area is associated with aggregated spending behaviors.

A system for identifying spending behaviors in a geographic area includes a database, a receiving device, and a processing device. The database is configured to store a plurality of geographic centroids, wherein each geographic centroid corresponds to a centroid of a predefined geographic area. The receiving device is configured to receive a plurality of financial transactions involving each consumer of a plurality of consumers. The processing device is configured to: identify a geographic location of each financial transaction of the plurality of financial transactions; calculate, for each consumer of the plurality of consumers, a purchase centroid of the financial transactions involving the consumer based on a centroid of the identified geographic location of each of the financial transactions involving the consumer; analyze, for each consumer, spending behaviors based on the financial transactions involving the consumer; associating the analyzed spending behavior for each consumer with the corresponding purchase centroid; associate, in the database, the analyzed spending behaviors for each purchase centroid with a predetermined number of geographic centroids based on the distance from the purchase centroid to each of the predetermined number of geographic centroids; and aggregate, in the database, each of the spending behaviors associated with each geographic centroid of the plurality of geographic centroids such that each corresponding geographic area is associated with aggregated spending behaviors.

System for Assigning Spend Behaviors to Geographic Areas

Figure 6:
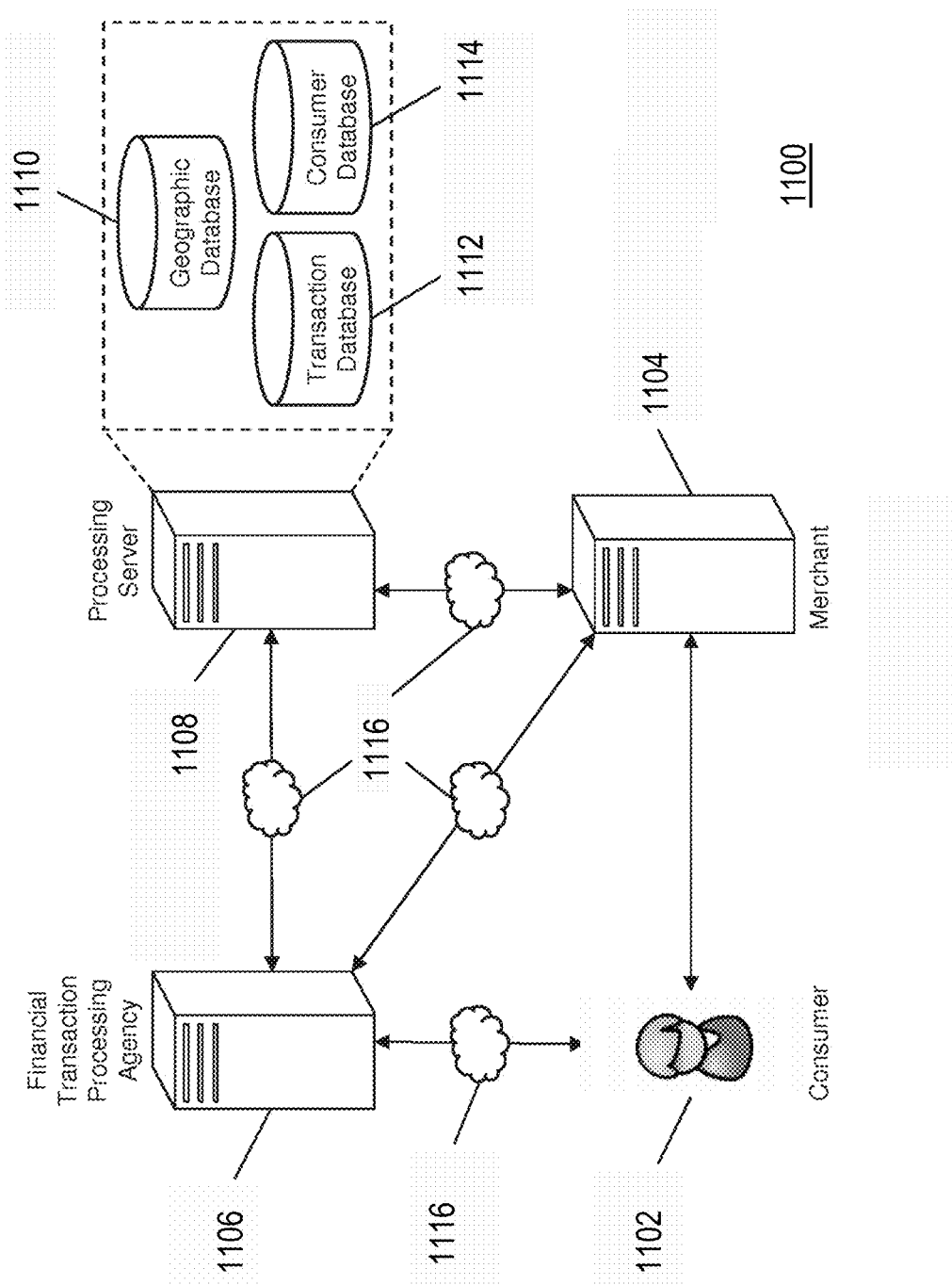
FIG. 6 is a block diagram illustrating a system for aggregating consumer spending behaviors in accordance with exemplary embodiments of U.S. patent application Ser. No. 13/721,216.

FIG. 6 illustrates a system 1100 for assigning consumer spend behaviors to a plurality of geographic areas based on purchase and geographic centroids. Several of the components of the system 1100 may communicate via a network 1116. The network 1116 may be any network suitable for performing the functions as disclosed herein and may include a local area network (LAN), a wide area network (WAN), a wireless network (e.g., Wi Fi), a mobile communication network, a satellite network, the Internet, fiber optic, coaxial cable, infrared, radio frequency (RF), or any combination thereof. Other suitable network types and configurations will be apparent to persons having skill in the relevant art.

The system 1100 may be used by a consumer 1102 who engages in a financial transaction with a merchant 1104. The financial transaction may be an in-person financial transaction (e.g., at a physical location of the merchant 1104) or may be performed remotely, such as via telephone, mail, or the Internet (e.g., "card not present" transactions). The financial transaction may be processed by a financial transaction processing agency 1106. The financial transaction processing agency 1106 may use any type of processing system configured to process financial transactions as part of a traditional four-party transaction processing system as apparent to persons having skill in the relevant art, such as MasterCard® or VISA®.

For example, the merchant 1104 may submit transaction details for the financial transaction to an acquiring bank, which may submit an authorization request to the financial transaction processing agency 1106. The financial transaction processing agency 1106 may contact an issuing bank that has issued a payment card used in the transaction to the consumer 1102 for approval of the transaction, which may subsequently be forwarded on to the acquiring bank and/or the merchant 1104. The financial transaction processing agency 1106 may identify and store transaction information for each financial transaction processed. Transaction information may include, for example, payment method, transaction amount, merchant identification, transaction location, merchant industry, transaction time and date, etc.

The merchant 1104 may have a desire to advertise to consumers, such as the consumer 1102, that have a frequency of transacting in the geographic area of a physical location of the merchant 1104. In order to identify these consumers, the merchant 1104 may submit a request to a processing server 1108. The processing server 1108, as discussed in more detail below, may receive transaction information from the financial transaction processing agency 1106 and store the received information in a transaction database 1112. In an exemplary embodiment, the transaction information received and stored in the transaction database 1112 may not include any personally identifiable information. In one embodiment, the processing server 1108 and the financial transaction processing agency 1106 may be a single entity.

The processing server 1108 may also include a geographic database 1110, configured to store geographic areas and their associated geographic centroids, as discussed in more detail below. The processing server 1108 may be configured to identify purchase centroids for consumers, by methods as discussed herein and apparent to persons having skill in the relevant art, based on associated transaction information stored in the transaction database 1112. The processing server 1108 may also be configured to analyze spend behaviors for consumers (e.g., the consumer 1102) based on the transaction information. The processing server 1108 may be further configured to identify a predetermined number of geographic centroids based on the distance from a purchase centroid to the corresponding geographic centroids, and associate the analyzed spend behaviors with the identified geographic areas. The corresponding data may be aggregated and used in order to identify consumers to respond to the request of the merchant 1104.

Processing Server

Figure 7:
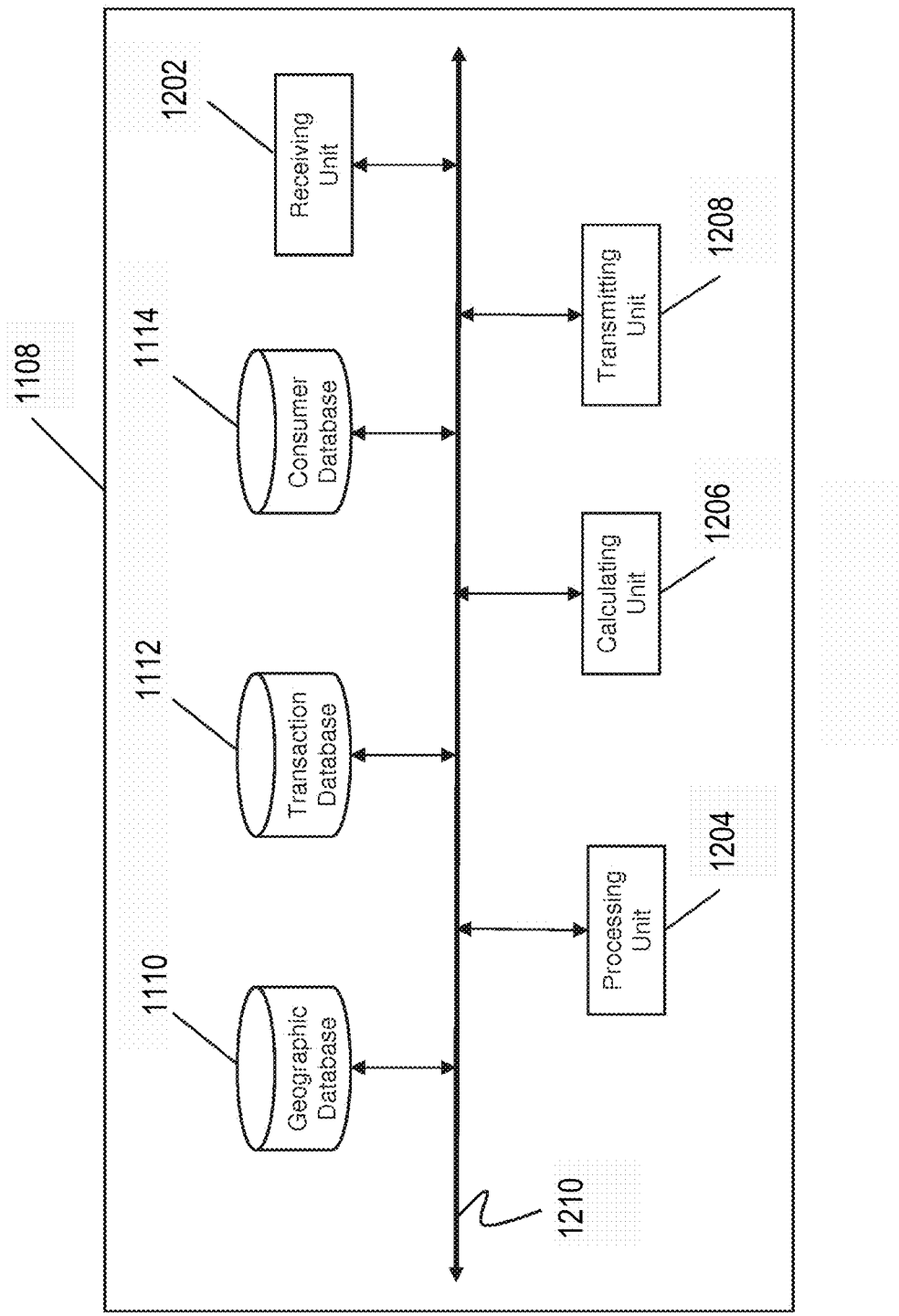
FIG. 7 is a block diagram illustrating the processing server of the system of FIG. 6 in accordance with exemplary embodiments of U.S. patent application Ser. No. 13/721,216.

FIG. 7 illustrates an embodiment of the processing server 1108. The processing server 1108 may be any kind of server configured to perform the functions as disclosed herein, such as the computer system illustrated in FIG. 5 and described in more detail elsewhere herein. The processing server 1108 may include the geographic database 1110, the transaction database 1112, a consumer database 1114, a receiving unit 1202, a processing unit 1204, a calculating unit 1206, and a transmitting unit 1208. Each of the components may be connected via a bus 1210. Suitable types and configurations of the bus 1210 will be apparent to persons having skill in the relevant art.

Data stored in the geographic database 1110, the transaction database 1112, and the consumer database 1114 (the "databases") may be stored on any type of suitable computer readable media, such as optical storage (e.g., a compact disc, digital versatile disc, blu-ray disc, etc.) or magnetic tape storage (e.g., a hard disk drive). The databases may be configured in any type of suitable database configuration, such as a relational database, a structured query language (SOL) database, a distributed database, an object database, etc. Suitable configurations and database storage types will be apparent to persons having skill in the relevant art. The databases may each be a single database, or may comprise multiple databases which may be interfaced together (e.g., physically or via a network, such as the network 1116).

The geographic database 1110, as discussed in more detail below, may be configured to store information regarding a plurality of geographic areas and corresponding geographic centroids. A geographic centroid may be a centroid of the corresponding geographic area as identified and/or calculated (e.g., by the calculating unit 1206) by the processing server 1108. Methods for calculating or identifying the centroid of an area will be apparent to persons having skill in the relevant art and may include a plumb line or balancing method, geometric decomposition, integral formula, etc.

The transaction database 1112 may be configured to store transaction information corresponding to a plurality of financial transactions including a plurality of consumers. In an exemplary embodiment, the transaction information may contain no personally identifiable information. The transaction information may include any information suitable for performing the functions as disclosed herein, such as transaction location, merchant identification, transaction time and/or date, transaction amount, payment method, etc. The consumer database 1114 may be configured to store consumer profile information for a plurality of consumers as discussed in more detail below.

The receiving unit 1202 may be configured to receive transaction information for a plurality of transactions, which may be stored (e.g., via the processing unit 1204) in the transaction database 1112. In embodiments where the processing server 1108 may also operate as the financial transaction processing agency 1106, the receiving unit 1202 may be further configured to receive authorization requests for financial transactions. The receiving unit 1202 may also be configured to receive requests from merchants (e.g., the merchant 1104) for spending behaviors in at least one geographic area.

The processing unit 1204 may be configured to identify a geographic location of each financial transaction stored in the transaction database 1112. In one embodiment, the geographic location may be directly included in the transaction information. In another embodiment, the processing unit 1204 may identify a geographic location associated with the merchant included in the financial transaction (e.g., by utilizing a lookup table of geographic locations and merchant identification numbers). Other methods for identifying geographic locations of financial transactions will be apparent to persons having skill in the relevant art, such as receiving the geographic location from a mobile communication device used in the financial transaction (e.g., for payment via an electronic wallet).

The calculating unit 1206 may be configured to calculate a purchase centroid for each consumer based on the identified geographic locations of the financial transactions included the respective consumer, as discussed in more detail below with respect to FIG. 11. The processing unit 1204 may be configured to store the calculated purchase centroid in the consumer database 1114 in a consumer data entry corresponding to the associated consumer.

The processing unit 1204 may be further configured to analyze, for each consumer, spending behaviors based on the financial transactions including the consumer and stored in the transaction database 1112. Spending behaviors may include, for example, propensity to spend, propensity to spend in a particular industry, propensity to spend at a particular merchant, transaction frequency, transaction frequency in a particular industry or at a particular merchant, regular spend amount, regular spend amount in a particular industry or at a particular merchant, propensity to spend at specific dates and/or times, and other behaviors as will be apparent to persons having skill in the relevant art. The processing unit 1204 may then associate the analyzed spending behaviors to the consumer's corresponding purchase centroid.

The processing unit 1204 (e.g., or the calculating unit 1206) may be further configured to identify a predetermined number of geographic areas based on the distance from a purchase centroid to the corresponding geographic centroid, and associate the corresponding spend behaviors to the geographic area. It will be apparent to persons having skill in the relevant art that the predetermined number of geographic areas may vary from application to application. For example, in some industries where consumers are less likely to commute a long distance to transact, such as grocery shopping, the predetermined number may be based on a particular distance (e.g., 5 miles for a rural region). In industries where consumers are more likely to commute, such as for specialty items, the predetermined number may be based on a further distance (e.g., 25 miles). In some instances, the predetermined number of geographic areas may be an integer number, such as the five closest geographic areas.

The processing unit 1204 may also be configured to aggregate the spending behaviors associated with a geographic area in order to identify an overall (e.g., average) spending behavior for consumers that regularly transact in or near the geographic area. The transmitting unit 1208 may be configured to transmit the aggregated spending behaviors to the merchant 1104, such as in response to a request for spending behaviors. The aggregated spending behaviors may be for the geographic area including the merchant 1104, or the geographic area may be selected based on the corresponding spending behaviors. For example, the merchant 1104 may request the geographic area for all consumers with a specified propensity to spend in its respective industry, so that the merchant 1104 can advertise to the consumers in that geographic area.

Consumer and Geographic Databases

Figure 8:
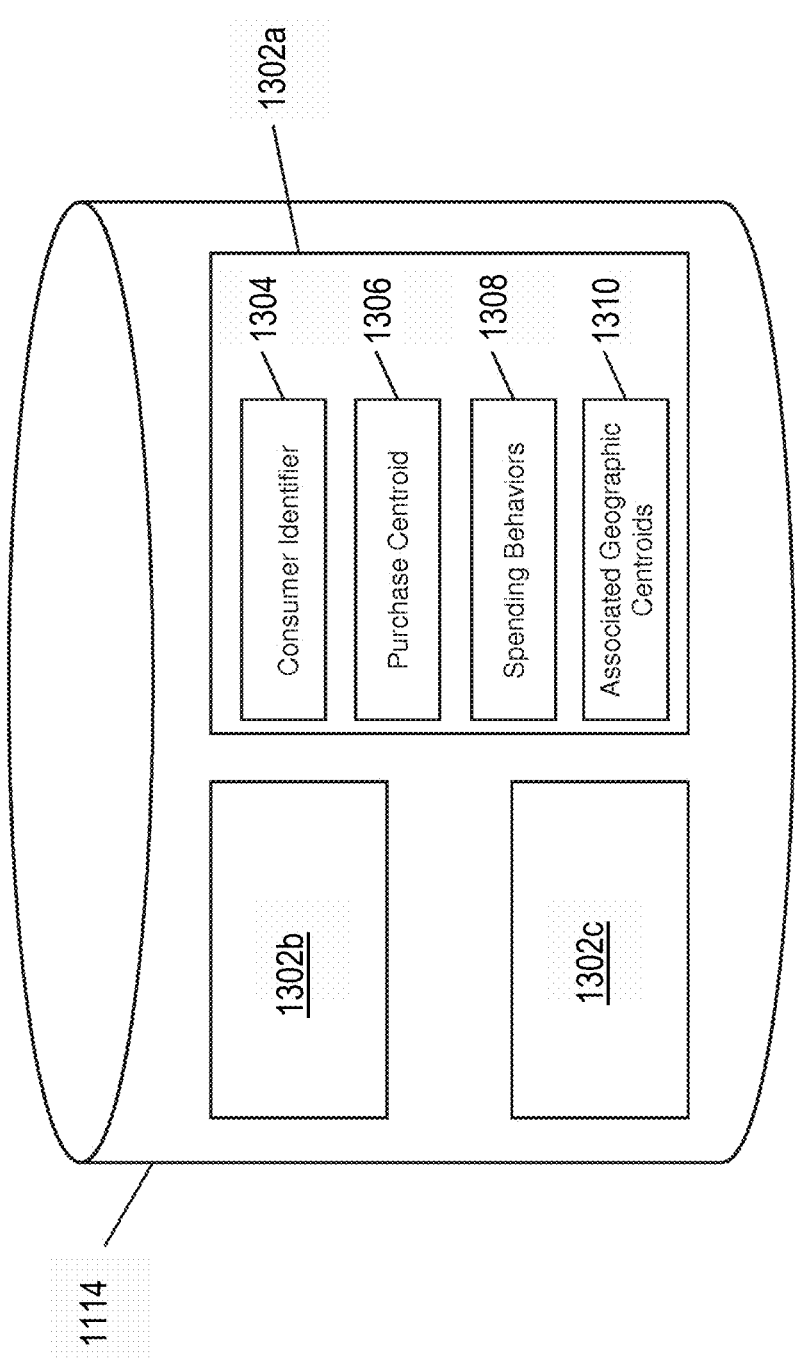
FIG. 8 is a block diagram illustrating the consumer database of FIG. 6 in accordance with exemplary embodiments of U.S. patent application Ser. No. 13/721,216.

FIG. 8 illustrates the consumer database 1114 of the processing server 1108. The consumer database 1114 may include a plurality of consumer data entries 1302, illustrated as consumer data entries 1302a, 1302b, and 1302c. Each consumer data entry 1302 may include at least a consumer identifier 1304, a purchase centroid 1306, spending behaviors 1308, and associated geographic centroids 1310. It will be apparent to persons having skill in the relevant art that the associated geographic centroids 1310 may be optional (e.g., and alternatively stored in the geographic database 1110).

The consumer identifier 1304 may be a unique value associated with a consumer (e.g., the consumer 1102) for identification of the consumer. In one embodiment, the consumer identifier 1304 may be an account number, such as for a payment card account. In another embodiment, the consumer identifier 1304 may be a unique value identified and/or generated by the processing server 1108 (e.g., via the processing unit 1204). The consumer identifier 1304 may be used in order to associate the consumer 1102 with the financial transactions including the consumer 1102 stored in the transaction database 1112.

The purchase centroid 1306 may be a purchase centroid associated with the consumer 1102 based on the geographic location of financial transactions including the consumer 1102, as described in more detail below. In an exemplary embodiment, the purchase centroid 1306 may be a geographic location represented using latitude and longitude. The spending behaviors 1308 may be spending behaviors associated with the consumer 1102 based on analysis of financial transactions including the consumer 1102 and stored in the transaction database 1112. Behaviors included in the spending behaviors 1308 may include propensity to spend, propensity to spend in a particular industry, etc. as discussed above.

The associated geographic centroids 1310 may include geographic centroids (e.g., or their corresponding geographic areas) for which the consumer's purchase centroid 1306 is associated. In some embodiments, the associated geographic centroids 1310 may only include a single geographic centroid (e.g., the closest geographic centroid to the purchase centroid 1306). In other embodiments, the number of geographic centroids included in the associated geographic centroids 1310 may be based on a variety of factors, such as requested number of areas, spending behaviors, geographic area selection, etc.

Figure 9:
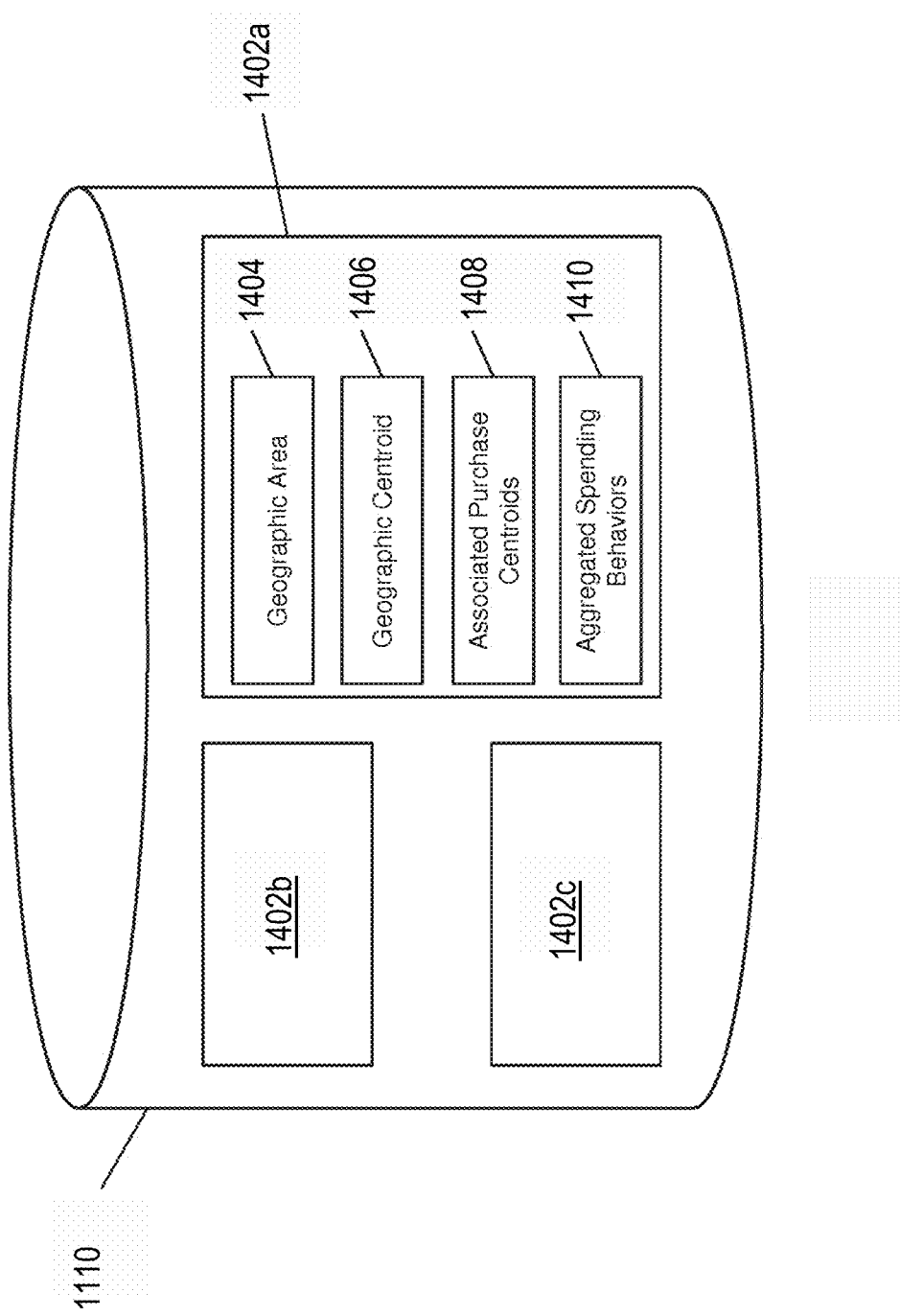
FIG. 9 is a block diagram illustrating the geographic database of FIG. 6 in accordance with exemplary embodiments of U.S. patent application Ser. No. 13/721,216.

FIG. 9 is an illustration of the geographic database 1110 of the processing server 1108. The geographic database 1110 may include a plurality of geographic data entries 1402, illustrated as geographic data entries 1402a, 1402b, and 1402c. Each geographic data entry 1402 may include a geographic area 1404, a geographic centroid 1406, associated purchase centroids 1408, and aggregated spending behaviors 1410. Additional information that may be included in the geographic database 1110 will be apparent to persons having skill in the relevant art.

The geographic area 1404 may be any geographic area for which spending behaviors may be aggregated. For example, the geographic area 1404 may be a zip code or postal code, a county, a municipality, a shopping district, shopping center, or any other defined geographic area as will be apparent to persons having skill in the relevant art. In an exemplary embodiment, the geographic area 1404 may be defined using latitude and longitude. The geographic centroid 1406 may be the calculated or identified centroid of the geographic area 1404. Methods used for calculating or identifying the geographic centroid of an area will be apparent to persons having skill in the relevant art.

The associated purchase centroids 1408 may include all purchase centroids (e.g., or consumer data entries 1302 including the respective purchase centroids) associated with the geographic area 1404 as discussed herein. The aggregated spending behaviors 1410 may include an aggregation of spending behaviors for each of the consumer data entries 1302 corresponding to each purchase centroid 1306 in the associated purchase centroids 1408. As such, the aggregated spending behaviors 1410 may be a representation of the spending behavior of consumers that regularly transact in or near the geographic area 1404.

Geographic and Purchase Centroids

Figure 10:
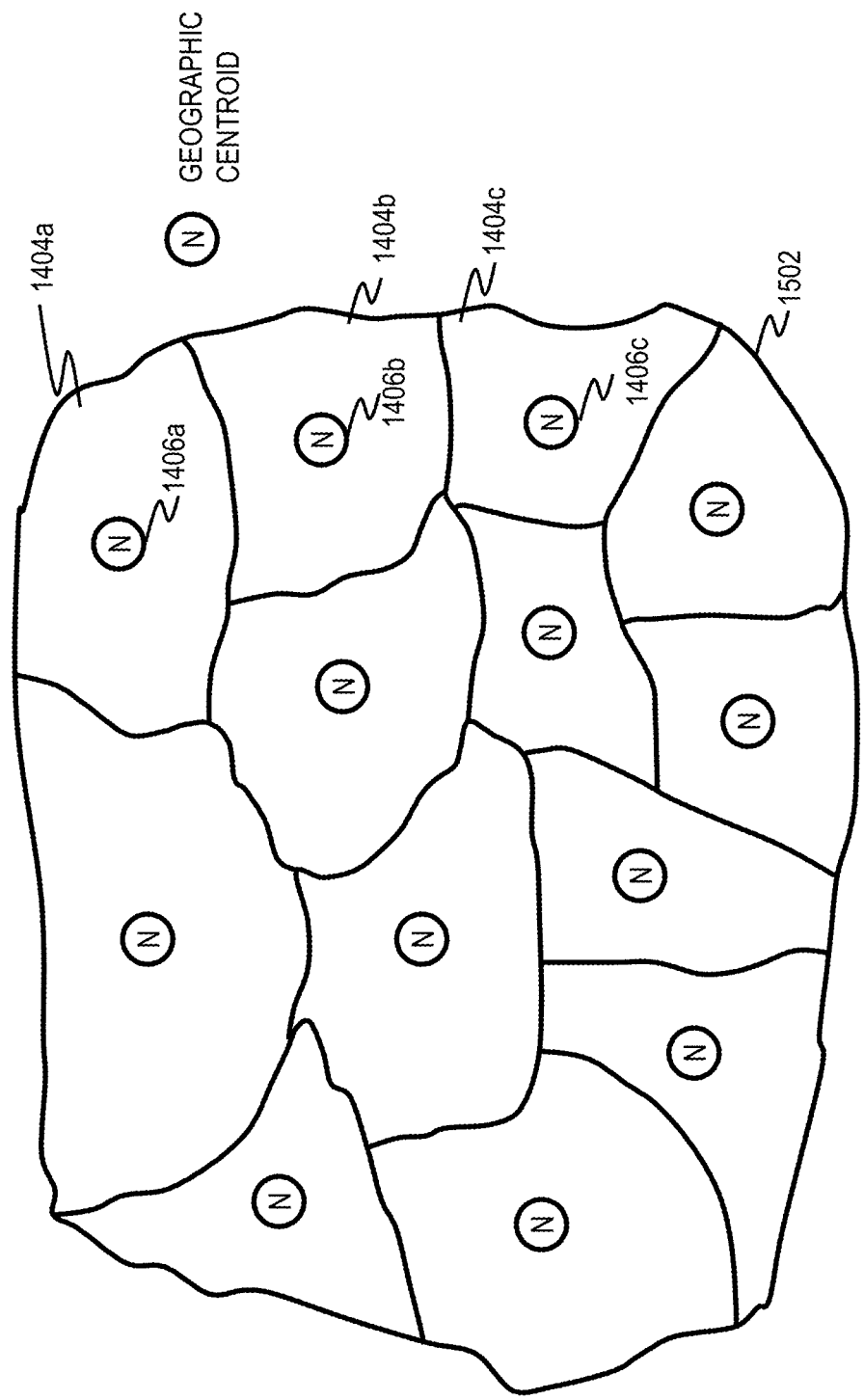
FIG. 10 is a diagram illustrating a plurality of geographic areas and corresponding geographic centroids in accordance with exemplary embodiments of U.S. patent application Ser. No. 13/721,216.

FIG. 10 is an illustration of an area 1502 that includes a plurality of geographic areas 1404, illustrated as geographic area 1404a, 1404b, and 1404c. As discussed previously, each geographic area 1404 may have a corresponding geographic centroid 1406. The geographic centroid 1406 may be the centroid, or the geometric center, of the corresponding geographic area 1404. As illustrated in FIG. 10, geographic areas 1404a, 1404b, and 1404c each include a corresponding geographic centroid 1406a, 1406b, and 1406c, respectively.

Figure 11:
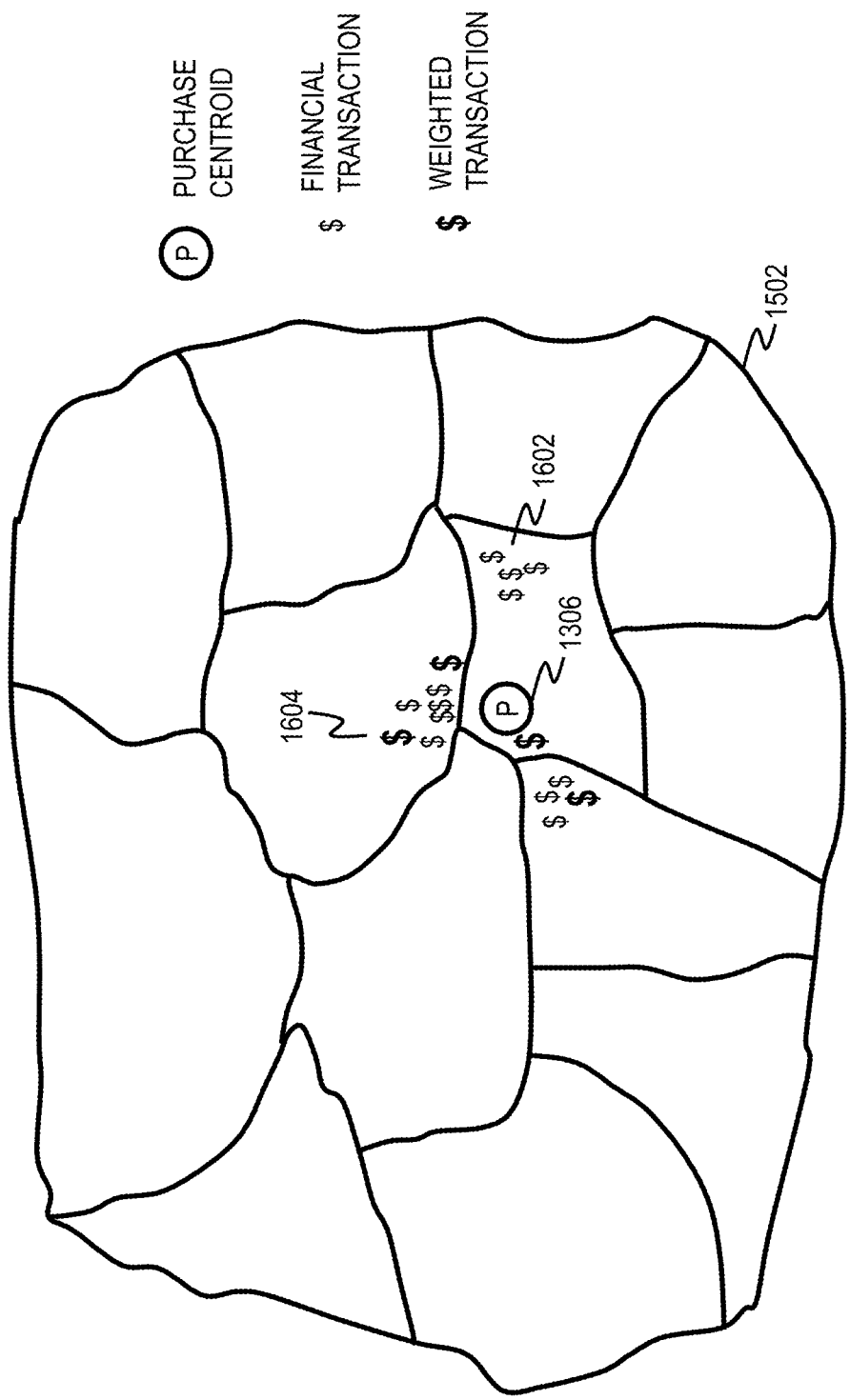
FIG. 11 is a diagram illustrating a plurality of financial transactions and identification of a purchase centroid in accordance with exemplary embodiments of U.S. patent application Ser. No. 13/721,216.

FIG. 11 is an illustration of the area 1502 as displaying a plurality of financial transactions 1602. The plurality of financial transactions 1602 may include those financial transactions that include a specific consumer 1102, such as based on the associated consumer identifier 1304. The financial transactions 1602 may be displayed based on their geographic location, which may be utilized using methods as discussed herein in order to calculate or identify the purchase centroid 1306 corresponding to the financial transactions.

In some embodiments, the financial transactions 1602 may include weighted financial transactions, such as the weighted transactions 1604. Weighted transactions may be financial transactions that have greater weight when calculating or identifying the purchase centroid 1306. A transaction may have a greater weight depending on the circumstances and application. For example, transactions may be weighted based on the transaction amount, such that large transactions are considered more heavily than smaller transactions for the calculation of the purchase centroid 1306. Similarly, if spending behaviors are analyzed for a particular industry, financial transactions that include a merchant within that industry may be viewed as weighted transactions 1604. In some instances, all of the financial transactions 1602 may include only those transactions of a specific industry. Other considerations for the weighting of financial transactions will be apparent to persons having skill in the relevant art, such as time of day, day of the week, season (e.g., summer spending as opposed to winter spending), etc.

Figure 12:
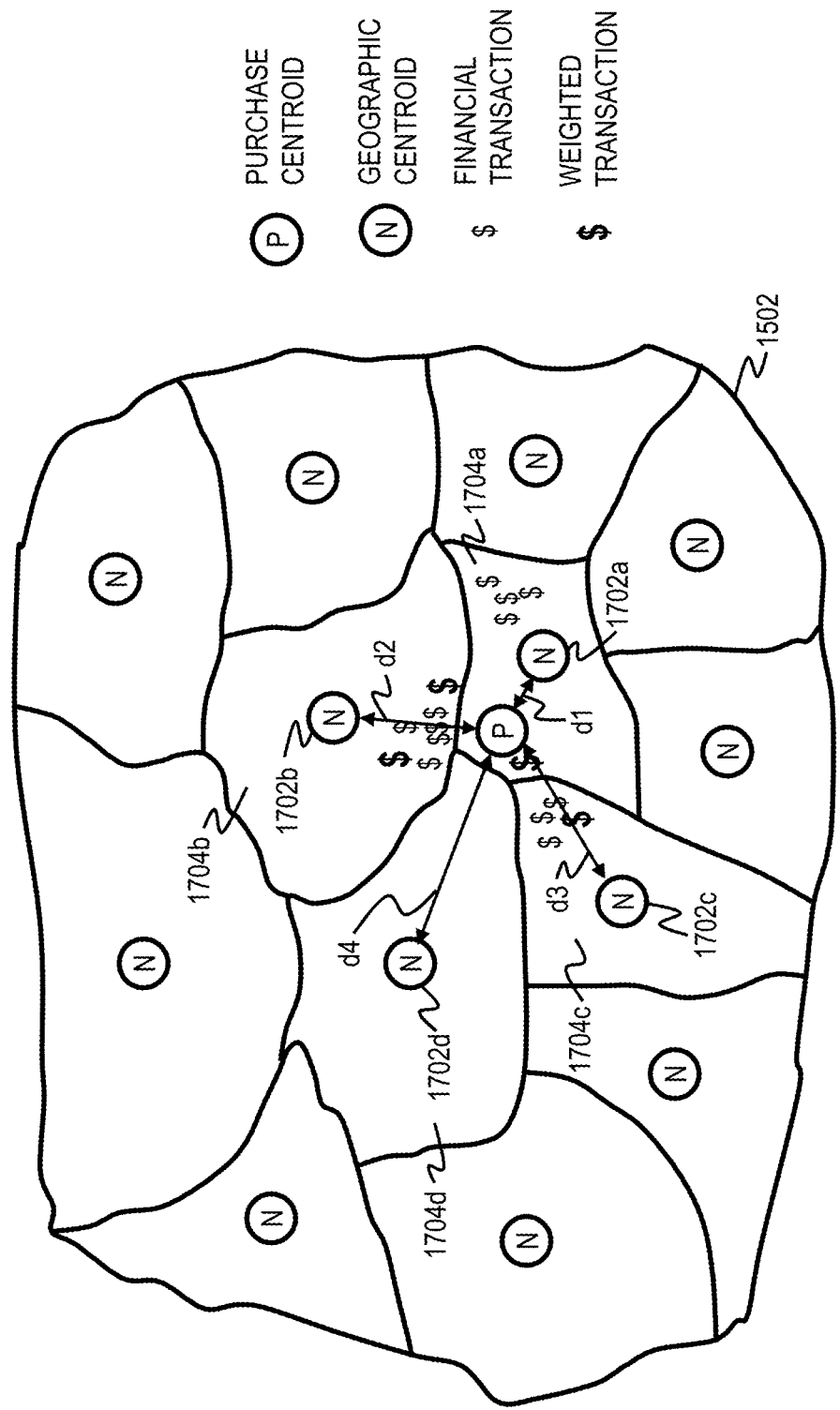
FIG. 12 is a diagram illustrating the identification of a predetermined number of geographic centroids in accordance with exemplary embodiments of U.S. patent application Ser. No. 13/721,216.

FIG. 12 illustrates the area 1502 and the identification of geographic centroids 1406 to be associated with the purchase centroid 1306 associated with the consumer 1102. As illustrated in FIGS. 10 and 11, in the area 1502, the geographic centroid 1406 has been identified and the purchase centroid 1306 for the financial transactions 1602 has been identified. Based on this information, as discussed herein, a predetermined number of geographic centroids 1406 may be identified based on the distance from the purchase centroid 1306 to the corresponding geographic centroid 1406. In one embodiment, the predetermined number of geographic centroids may be 4, or may be all geographic centroids 1406 within a distance d4 from the purchase centroid 1306, as illustrated in FIG. 12.

Based on the distances d1, d2, d3, and d4, the plurality of geographic centroids 1702 may be identified as those geographic centroids 1702 that fit the criteria for establishing the predetermined number of centroids. The processing server 1204 may then update the corresponding consumer data entry 1302 to reflect geographic centroids 1702a, 1702b, 1702c, and 1702d as the associated geographic centroids 1310 associated with the purchase centroid 1306. In addition, the processing server 1204 may update the corresponding geographic data entry 1402 including each of the identified geographic areas 1704a, 1704b, 1704c, and 1704d as including the purchase centroid 1306 in the respective associated purchase centroids 1408.

Method for Analyzing and Aggregating Spending Behaviors

Figure 13:
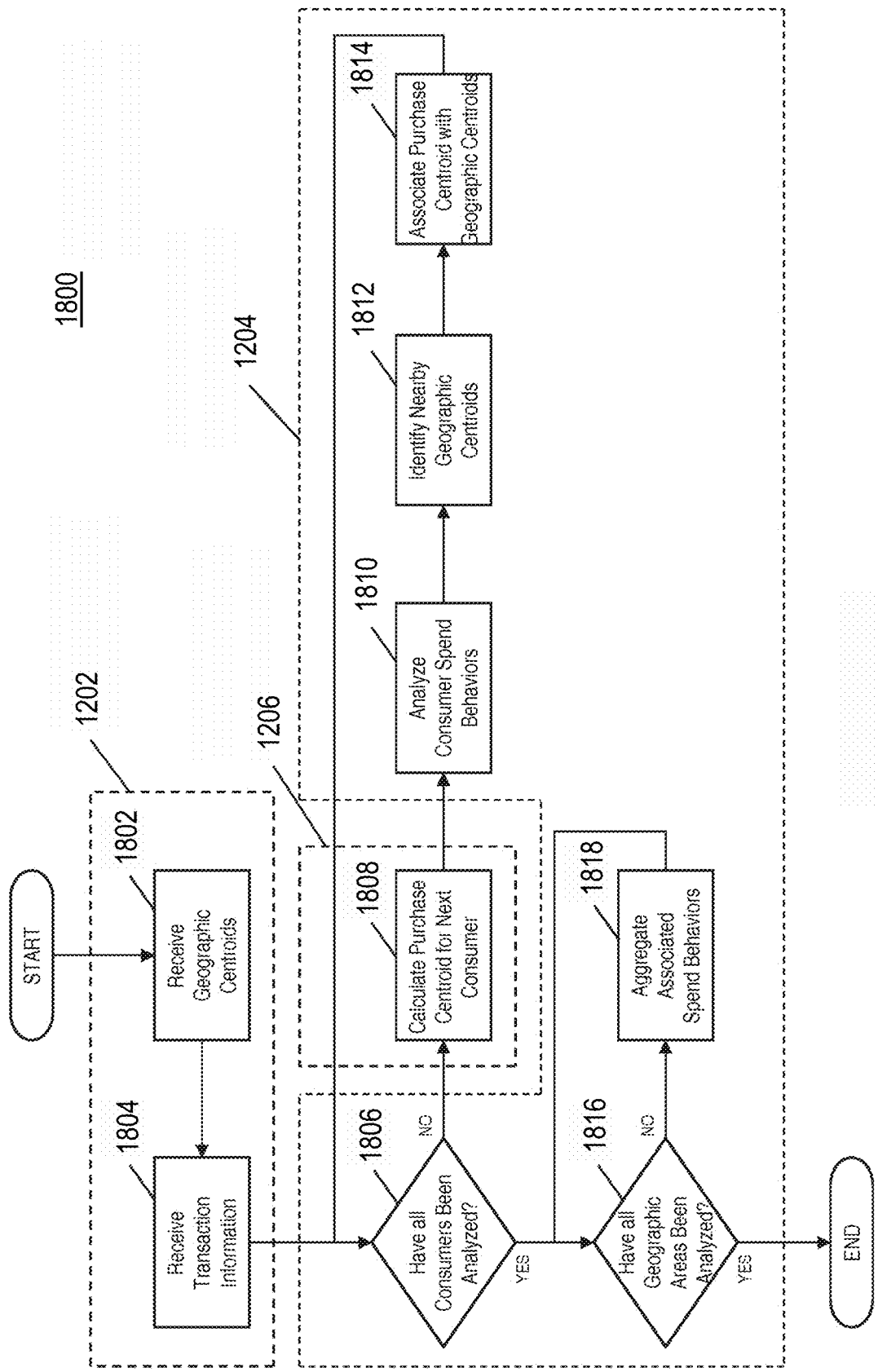
FIG. 13 is a flow chart illustrating a method for aggregating consumer spending behaviors in geographic areas in accordance with exemplary embodiments of U.S. patent application Ser. No. 13/721,216.

FIG. 13 illustrates a method 1800 for the analyzing and aggregation of spending behaviors for a geographic area.

In step 1802, a plurality of geographic centroids 1406 may be received. Each geographic centroid 1406 may be associated with a predefined geographic area 1404. In one embodiment, the geographic centroids 1406 may be stored in the geographic database 1110, as discussed above. In one embodiment, the geographic areas 1404 may be based on a zip code or postal code, may be defined by latitude or longitude boundaries, may be based on municipal boundaries, or a combination thereof.

In step 1804, transaction information for a plurality of financial transactions including a plurality of consumers may be received (e.g., and subsequently stored in the transaction database 1112). Steps 1802 and 1804 may be performed by the receiving unit 1202. In some embodiments, step 1802 may include only the receipt of a plurality of geographic areas 1404, from which the corresponding geographic centroids 1406 may be calculated (e.g., by the calculating unit 1206).

In step 1806, it may be determined (e.g., by the processing unit 1204) if all consumers have been analyzed. If not, then, in step 1808, the calculating unit 1206 may calculate the purchase centroid 1306 for the next consumer (e.g., corresponding to the next unanalyzed consumer data entry 1302). Methods for calculating the purchase centroid 1306 will be apparent to persons having skill in the relevant art as discussed herein, such as identifying the geographic location of each financial transaction including the consumer and calculating the purchase centroid 1306 using known centroid calculation methods.

In step 1810, the processing unit 1204 may analyze the financial transactions including the consumer to determine consumer spend behaviors. In some embodiments, the consumer spend behaviors determined may be based on the application of the data. For example, the consumer spend behaviors may include spend propensity for a specific industry, such as the industry of the merchant 1104 requesting the information. The processing unit 1204 may store the analyzed spend behaviors in the corresponding consumer data entry 1302 in the consumer database 1114 as the included spending behaviors 1308. In step 1812, the processing unit 1204 may identify a predetermined number of geographic centroids near the purchase centroid 1306. In some embodiments, the predetermined number of geographic centroids may be based on distance to the purchase centroid (e.g., all geographic centroids within 20 miles), based on a specific number (e.g., the 5 closest geographic centroids) or other criteria as will be apparent to persons having skill in the relevant art.

In step 1814, the processing unit 1204 may associate the purchase centroid 1306 with the identified geographic centroids. Associating the purchase centroid 1306 with the identified geographic centroids may include storing, in the corresponding consumer data entry 1302, the associated geographic centroids 1310, or storing, in the corresponding geographic data entry 1402 for each identified geographic centroid, the purchase centroid 1306 as an associated purchase centroid 1408. Then, the method 1800 may return to step 1806 and again determine if all consumers have been analyzed.

Once all consumers have been analyzed, then, in step 1816, the processing unit 1204 may determine if all geographic areas 1404 (e.g., based on the corresponding geographic data entries 1402) have been analyzed. If they have not, then, in step 1818, the processing unit 1204 may aggregate the spending behaviors associated with each geographic data entry 1402. Aggregating the spending behaviors for each geographic data entry 1402 may include identifying the consumer data entry 1302 for each purchase centroid 1306 included in the associated purchase centroids 1408, and aggregating the corresponding spending behaviors 1308 for each identified consumer data entry 1302. In one embodiment, the processing unit 1204 may store the aggregated spending behaviors 1410 in the corresponding geographic data entry 1402. Following this, the processing unit 1204 may again determine, in step 1816, if all geographic areas 1404 have been analyzed. If all have been analyzed (e.g., spending behaviors aggregated for each geographic area 1404), then the method 1800 may be completed.

Exemplary Method for Assigning Spending Behaviors to Geographic Areas

Figure 14:
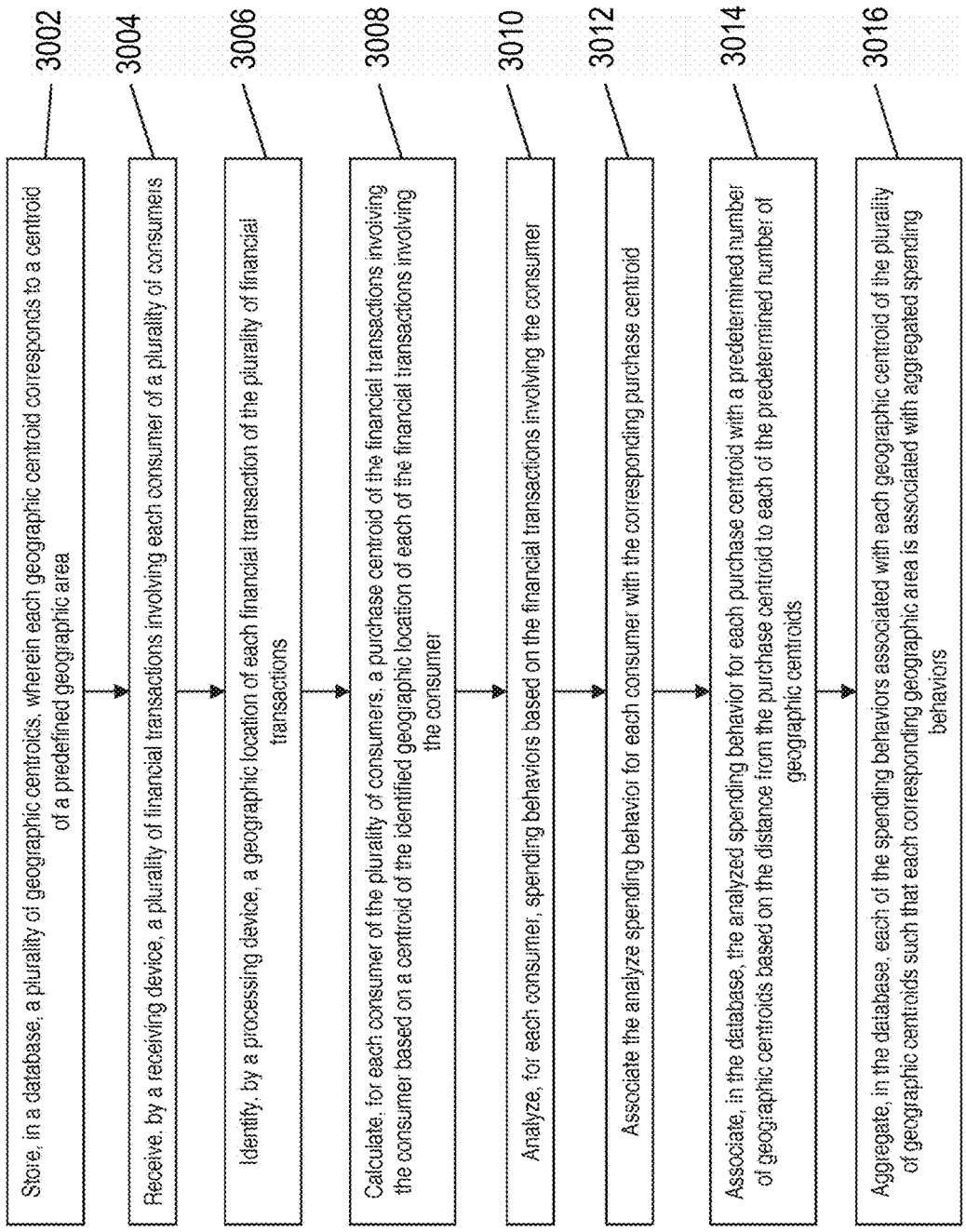
FIG. 14 is a flow chart illustrating an exemplary method for assigning consumer behaviors to geographic areas in accordance with exemplary embodiments of U.S. patent application Ser. No. 13/721,216.

FIG. 14 illustrates a method 3000 for assigning consumer spend behaviors to geographic areas via the use of purchase and geographic centroids.

In step 3002, a plurality of geographic centroids (e.g., geographic centroids 1406) may be stored in a database (e.g., the geographic database 1110), wherein each geographic centroid 1406 corresponds to a centroid of a predefined geographic area (e.g., geographic area 1404). In one embodiment, the predefined geographic area may be based on a zip code or a postal code. In another embodiment, the predefined geographic area may be defined by latitude and longitude measurements. In yet another embodiment, the predefined geographic area may be based on municipal boundaries.

In step 3004, a plurality of financial transactions including each consumer of a plurality of consumers may be received by a receiving device (e.g., the receiving unit 1202). In step 3006, a processing device (e.g., the processing unit 1204) may identify a geographic location of each financial transaction of the plurality of financial transactions. In one embodiment, identifying the geographic location of each financial transaction may include identifying, in a database, the latitude and longitude of a merchant point of sale included in the financial transaction. In another embodiment, identifying the geographic location of each financial transaction may include identifying the geographic location of a mobile communication device used as a payment method in the respective financial transaction.

In step 3008, a purchase centroid (e.g., the purchase centroid 1306) of the financial transactions involving a consumer may be calculated (e.g., by the calculating unit 1206) for each consumer of the plurality of consumers, based on a centroid of the identified geographic location of each of the financial transactions involving the consumer. In one embodiment, calculating the purchase centroid 1306 of the financial transactions may include weighing or filtering the financial transactions based on predetermined factors. In a further embodiment, the predetermined factors may include at least one of: merchant code or type, product category, transaction amount, transaction frequency, and geographic location of the transaction. In another embodiment, the plurality of financial transactions may include only financial transactions of a predetermined category. In a further embodiment, the predetermined category may be based on at least one of: time of day, day of the week, month, season, home location, employment location, merchant code, product category, industry code, and transaction amount. In some embodiments, multiple purchase centroids may be calculated for each consumer, such as purchase centroids for each of a number of predetermined categories.

In step 3010, spending behaviors (e.g., the spending behaviors 1308) for each consumer may be analyzed (e.g., by the processing unit 1204) based on the financial transactions including the consumer. In one embodiment, the spending behaviors 1308 may include at least one of: propensity to spend, propensity to spend in a particular industry, frequency of spending, amount of spending, industry preference, brand preference, and time of spending. In step 3012, the analyzed spending behavior 1308 for each consumer may be associated with the corresponding purchase centroid 1306. Further details of consumer spending analysis can be found, e.g., in U.S. Patent Publication 2013-0024242, "Protecting Privacy in Audience Creation" of Villars et al., expressly incorporated by reference herein in its entirety for all purposes.

In step 3014, the analyzed spending behavior 1308 for each purchase centroid 1306 may be associated, in the geographic database 1110, with a predetermined number of geographic centroids 1310 based on the distance from the purchase centroid 1306 to each of the predetermined number of geographic centroids 1310. In one embodiment, the predetermined number of geographic centroids 1310 may be based on a privacy concern. In a further embodiment, the privacy concern may be such that no consumer is personally identifiable. In another embodiment, the predetermined number of geographic centroids 1310 may include all geographic centroids 1406 in a specified distance radial from the purchase centroid 1306.

In step 3016, each of the spending behaviors 1308 associated with each geographic centroid 1406 of the plurality of geographic centroids 1406 may be aggregated, in the geographic database 1110, such that each corresponding geographic area 1404 may be associated with the aggregated spending behaviors (e.g., the aggregated spending behaviors 1410).

The calculation of purchase centroids on the basis of financial transactions may be beneficial for merchants and advertisers by identifying consumers and spending behaviors for specific locations. It will be apparent to persons having skill in the relevant art that centroids may also be calculated on additional activities and my not be strictly limited to financial transactions. For example, centroids may be calculated based on social network activities (e.g., locations when a consumer posts to Facebook®, Twitter®, FourSquare®, etc.), locations where a consumer sends messages (e.g., short message service messages) or conducts calls from a mobile device, etc.

The identification of purchase centroids and associated spending behaviors may also have additional applications and be beneficial for advertisers and merchants in addition to those discussed herein, as will be apparent to persons having skill in the relevant art. For example, the analysis of purchase centroids based on dates may identify when a consumer moves from one location to another, which may present the consumer as ideal for receiving advertising for offers or services in a new location. Similarly, purchase centroids may identify a consumer that lives in multiple locations (e.g., a seasonal home), which may benefit merchants by knowing that the consumer need only be advertised to for certain periods. Additional uses for purchase centroids and aggregated spending behaviors as discussed herein will be apparent to persons having skill in the relevant art.

Techniques consistent with the present disclosure provide, among other features, systems and methods for assigning spend behaviors to geographic areas.

What is claimed is:

1. A method comprising the steps of:
   with a healthcare database module, embodied on a non-transitory computer-readable storage medium, executing on at least one hardware processor, accessing health-related data;
   with a transaction database module, embodied on said non-transitory computer-readable storage medium, executing on said at least one hardware processor, querying an ISO 8583 payment card network database for payment card transaction records corresponding to respective purchases made using at least one payment card, wherein said ISO 8583 payment card network database of payment card transaction records does not include any personally identifiable information;
   inferring geographic locations of at least a portion of said payment card transaction records;
   with a linkage module, embodied on said non-transitory computer-readable storage medium, executing on said at least one hardware processor, geographically linking at least a portion of said health-related data to said portion of said payment card transaction records to obtain linked data by querying said health-related data and said database of payment card transaction records, based on said inferred geographic locations;
   with a supervised learning module, embodied on said non-transitory computer-readable storage medium executing on said at least one hardware processor, carrying out statistical analysis on said linked data; and
   with a user interface module, embodied on said non-transitory computer-readable storage medium, executing on said at least one hardware processor, making anonymized aggregated results of said statistical analysis available to at least one appropriate party in a privacy-compliant manner.

2. The method of claim 1, wherein:
   in said step of making said results of said statistical analysis available to said at least one appropriate party, said results comprise an epidemiological predictor; and said epidemiological predictor comprises at least one of a correlation and a prediction regarding visiting a certain geographic location and incidence of a certain disease.

3. An apparatus comprising:
a memory;
at least one processor operatively coupled to said memory; and
a persistent storage device operatively coupled to said memory and storing in a non-transitory medium instructions, which comprise a healthcare database module, a transaction database module, a linkage module, a supervised learning module; and a user interface module, wherein when loaded into said memory said instructions cause said at least one processor to be operative to:
with said healthcare database module, access health-related data;
with said transaction database module, query an ISO 8583 payment card network database for payment card transaction records corresponding to respective purchases made using at least one payment card, wherein said ISO 8583 payment card network database of payment card transaction records does not include any personally identifiable information;
infer geographic locations of at least a portion of said payment card transaction records;
with said linkage module, geographically link at least a portion of said health-related data to at least a portion of said payment card transaction records to obtain linked data by querying said health-related data and said database of payment card transaction records, based on said inferred geographic locations;
with said supervised learning module, carry out statistical analysis on said linked data; and
with said user interface module, make anonymized aggregated results of said statistical analysis available to at least one appropriate party in a privacy-compliant manner.

4. The apparatus of claim 3, wherein:
said results comprise an epidemiological predictor; and
said epidemiological predictor comprises at least one of a correlation and a prediction regarding visiting a certain geographic location and incidence of a certain disease.

5. A non-transitory computer readable medium comprising computer executable instructions, which comprise a healthcare database module, a transaction database module, a linkage module, a supervised learning module; and a user interface module, wherein when executed by a computer said computer executable instructions cause the computer to perform the method of:
with said healthcare database module, accessing health-related data;
with said transaction database module, querying an ISO 8583 payment card network database for payment card transaction records corresponding to respective purchases made using at least one payment card, wherein said ISO 8583 payment card network database of payment card transaction records does not include any personally identifiable information;
inferring geographic locations of at least a portion of said payment card transaction records;
with said linkage module, geographically linking at least a portion of said health-related data to said portion of said payment card transaction records to obtain linked data by using structured query language (SQL) on said health-related data and said database of payment card transaction records, based on said inferred geographic locations;
with said supervised learning module, carrying out statistical analysis on said linked data; and
with said user interface module, making anonymized aggregated results of said statistical analysis available to at least one appropriate party in a privacy-compliant manner.

6. The non-transitory computer readable medium of claim 5, wherein:
in said method step of making said results of said statistical analysis available to said at least one appropriate party, said results comprise an epidemiological predictor; and
said epidemiological predictor comprises at least one of a correlation and a prediction regarding visiting a certain geographic location and incidence of a certain disease.

* * * * *